US012636145B2

(12) United States Patent
Rzany et al.

(10) Patent No.: US 12,636,145 B2
(45) Date of Patent: May 26, 2026

(54) METHOD FOR THE PRODUCTION OF CROSSLINKED AND OPTIONALLY SHAPED TISSUE WITH SELECTIVE ADJUSTMENT OF THICKNESS, SHAPE AND/OR FLEXIBILITY

(71) Applicant: BIOTRONIK AG, Buelach (CH)

(72) Inventors: Alexander Rzany, Nuremberg (DE); Christine Mueller, Erlangen (DE); Nina Foh, Forchheim (DE); Judith Flore Solowiej, Neunkirchen am Brand (DE); Bernhard Hensel, Erlangen (DE)

(73) Assignee: BIOTRONIK AG, Buelach (CH)

( * ) Notice: Subject to any disclaimer, the term of this patent is extended or adjusted under 35 U.S.C. 154(b) by 550 days.

(21) Appl. No.: 18/248,445

(22) PCT Filed: Oct. 28, 2021

(86) PCT No.: PCT/EP2021/080040
§ 371 (c)(1),
(2) Date: Apr. 10, 2023

(87) PCT Pub. No.: WO2022/090420
PCT Pub. Date: May 5, 2022

(65) Prior Publication Data
US 2023/0390050 A1 Dec. 7, 2023

(30) Foreign Application Priority Data
Oct. 30, 2020 (EP) .................................... 20205069

(51) Int. Cl.
*A61F 2/24* (2006.01)
*A61L 27/36* (2006.01)
(52) U.S. Cl.
CPC ........ *A61F 2/2415* (2013.01); *A61L 27/3691* (2013.01)

(58) Field of Classification Search
CPC ........ A61F 2/2415; A61F 2/2412; A61F 2/06; A61F 2/07; A61L 27/3691
See application file for complete search history.

(56) References Cited
U.S. PATENT DOCUMENTS 5,733,337 A * 3/1998 Carr, Jr. .................. A61L 27/58
623/1.53
2002/0095218 A1* 7/2002 Carr, Jr. ................ A61L 2/0088
623/23.72
(Continued)

FOREIGN PATENT DOCUMENTS

EP 3156083 A1 9/2016

OTHER PUBLICATIONS

International Search Report from the corresponding International Patent Application No. PCT/EP2021/080040, dated Jan. 20, 2022.

*Primary Examiner* — Suzette J Gherbi
(74) *Attorney, Agent, or Firm* — Greer, Burns & Crain, Ltd.; Steven P. Fallon

(57) ABSTRACT

A method for chemically crosslinking and optionally shaping (including thickness reduction) substantially non-crosslinked tissue, in particular biological tissue, using a permeable material layer. The method can be used in combination with a stepless pressure load/compression on the tissue, so as to always allow fluid transport into and out of the tissue to be treated under the chemical cross-linking; along the lines of drainage. The method can be carried out under different pressure loads/compressions, in particular in order to specifically influence the resulting tissue properties, and, for example, to bring about a homogeneous thickness distribution of the tissue and/or to deliberately and specifically place inhomogeneities, if desired. Furthermore, the method allows the introduction/imprinting of a consistent three-
(Continued)

dimensional shape into the tissue to be treated, e.g. of inhomogeneities in the thickness of the tissue.

21 Claims, 8 Drawing Sheets

(56)  References Cited

U.S. PATENT DOCUMENTS

| | | | |
|---|---|---|---|
| 2007/0050014 A1* | 3/2007 | Johnson | A61F 2/2475 |
| | | | 623/2.13 |
| 2008/0097601 A1* | 4/2008 | Codori-Hurff | A61F 2/12 |
| | | | 623/7 |
| 2010/0011564 A1 | 1/2010 | Millwee et al. | |
| 2019/0247180 A1* | 8/2019 | Limem | A61F 2/12 |
| 2021/0267756 A1* | 9/2021 | Morin | A61L 31/146 |
| 2021/0353408 A1* | 11/2021 | Chen | A61F 2/2412 |
| 2022/0071920 A1* | 3/2022 | McKean | A61L 27/18 |
| 2023/0390050 A1* | 12/2023 | Rzany | A61F 2/2412 |
| 2024/0366829 A1* | 11/2024 | Bassett | A61L 15/44 |
| 2025/0205391 A1* | 6/2025 | Rzany | A61L 27/58 |

* cited by examiner

UTT PP

PP free fixation 16     15

17

18

METHOD FOR THE PRODUCTION OF CROSSLINKED AND OPTIONALLY SHAPED TISSUE WITH SELECTIVE ADJUSTMENT OF THICKNESS, SHAPE AND/OR FLEXIBILITY

PRIORITY CLAIM

This application is a 35 U.S.C. 371 US National Phase and claims priority under 35 U.S.C. § 119, 35 U.S.C. 365(b) and all applicable statutes and treaties from prior PCT Application PCT/EP2021/080040, which was filed Oct. 28, 2021, which application claimed priority from European Application Serial Number 20205069.6, which was filed Oct. 30, 2020.

FIELD OF THE INVENTION

The invention concerns cross-linking of substantially non-crosslinked tissue, including biological tissue. An example application of the invention is to make Transcatheter aortic valve implantation ("TAVI"), or transcatheter aortic valve replacement ("TAVR"), or percutaneous aortic valve replacement ("PAVR") implants.

BACKGROUND

Transcatheter aortic valve implantation ("TAVI"), or transcatheter aortic valve replacement ("TAVR"), or percutaneous aortic valve replacement ("PAVR") is a minimally invasive procedure in which an artificial aortic valve prosthesis is placed and released within the native aortic valve in a collapsed (crimped; compressed) state.

The implant usually consists of individual, manually sutured, collagen-containing tissue components integrated into a suitable self-expanding or mechanically expandable stent (e.g., balloon-expandable) or support structure. Through the typically complex and error-prone suturing method, a complex, three-dimensional tissue geometry is thereby created, which is essential for the functionality of the prosthesis. At the same time, the expert is aware that the numerous surgical nodes/sutures represent mechanical weak points that can potentially lead to failure of the implant, and thus can also sometimes cause severe complications in the patient.

There are basically three different types of prosthetic heart valves, especially aortic valve prostheses: Prostheses with mechanical valves, which are manufactured artificially, mostly from graphite coated with pyrolytic carbon; prostheses with valves made from biological tissue (or partly biological tissue locally reinforced by artificial fibers, if necessary), mostly pericardial tissue typically derived from animal sources (e.g., porcine or bovine); and valves made from artificial materials such as polymers. The heart valve formed from the biological tissue is generally secured in a base body (e.g., a solid plastic scaffold or a self-expanding stent or a balloon-expanding stent) and this is implanted in the position of the natural valve.

With decellularization, as many cellular components as possible are removed from the tissue and the biological material consists exclusively of extracellular matrix. In pericardial tissue, the extracellular matrix is predominantly formed from said collagen fibers. In order to achieve a biological material with the best possible mechanical properties and to prevent defense reactions of the receiving body, in the prior art the collagen fibers are crosslinked by a suitable crosslinking agent through the incorporation of chemical bonds.

The crosslinking agent specifically binds to free amino groups of the collagen fibers and forms chemically stable bonds between the collagen fibers. In this way, a long-term stable biological material is formed from the three-dimensionally arranged collagen fibers, which, moreover, is no longer recognized as foreign biological material. The three-dimensional crosslinking or linking of the individual collagen fibers via the crosslinking agent significantly increases the stability and stressability of the tissue. This is particularly crucial when used as the tissue of a heart valve, where the tissue must open and close as a valve every second.

According to the prior art, the tissue treated in this way is attached to a basic body (e.g., a hollow cylindrical nitinol stent), far predominantly by suturing using a plurality of surgical knots. The main body or scaffold is implantable by surgical techniques (mostly catheter-based). Frequently, the basic scaffold is self-expanding or mechanically expandable with the aid of a balloon, so that the prosthetic heart valve can be guided to the implantation site in a compressed state by a catheter and implanted within the natural valve.

In the prior art, such catheter-implantable prosthetic heart valves are usually stored in a storage solution, correspondingly in a moist state. The storage solution serves to sterilely stabilize the biological tissue. One conceivable storage solution is, for example, glutaraldehyde.

For implantation, the prosthetic heart valve must then be removed from the storage solution in the operating room and mounted on the catheter after several rinsing procedures. This assembly of the prosthetic heart valve only in the operating room is cumbersome and labor-intensive. In addition, the correct performance of the assembly depends on the skills of the particular surgical team.

In the case of various medical implants, the problem arises that after implantation, there is a leakage between the surface of the implant and an anatomical structure of the patient, for example, a vessel wall in which the implant was implanted. In the case of a prosthetic heart valve as a medical implant, for example, paravalvular leakage (PVL) may occur, limiting the performance of the prosthetic heart valve.

For example, a method of manufacturing a prosthetic heart valve that includes processing dried biological material has been disclosed in U.S. Pat. No. 8,105,375. According to the method disclosed therein, the biological tissue is fixed or crosslinked with an aldehyde-containing solution (e.g., glutaraldehyde or formaldehyde solution), and treated with at least one aqueous solution containing at least one biocompatible and non-volatile stabilizer prior to drying. Stabilizers include hydrophilic hydrocarbons with a plurality of hydroxyl groups, and examples include water-soluble sugar alcohols such as glycerol, or ethylene glycol or polyethylene glycol.

Basically, heart valve defects (Latin: vitia, singular: vitium) as medical indications for a prosthetic heart valve can be divided into stenoses and insufficiencies according to their functional disturbance. Of all valve vitias, calcifying aortic valve stenosis is the most common acquired valvular heart disease in Western industrialized nations and thus the most common medical indication for heart valve replacement (TAVI/TAVR/PAVR).

A conventionally manufactured transcatheter aortic valve prosthesis typically consists of up to six individual tissue parts/components that are manually sutured together in a usually extremely time-consuming and cost-intensive method, and then integrated into a stent or other frame structure. This gives the implant a complex, three-dimensional geometry that is essential for the functionality of the prosthesis. The mostly three freely supported, inwardly directed leaflets form semilunar pockets that passively effect valve closure. The additional skirt components (inner and/or outer skirt) attached to the stent/frame structure serve to prevent or seal against paravalvular leakage (PVL).

Thus, the tissue portion of a TAVI/TAVR valve usually consists of a total of six individual tissue components cut from cross-linked tissue patches. The three leaflet parts, which functionally effect the opening and closing of the prosthesis, are called "leaflets". The three so-called inner skirt parts are immovably attached internally to the stent/ frame structure in the final product and serve primarily to reduce paravalvular leakage. A shaping method, e.g. laser cutting or punching, is followed by a complex, multi-stage sewing method, which gives the valve implant its characteristic three-dimensional geometry. In some variants of the prior art, an outer skirt is additionally attached to the outside of the TAVI/TAVR valve, which is also mostly made of tissue and addresses PVL.

The entire suturing method of the valve is performed entirely manually under the microscope and is thus extremely time, cost and resource intensive. In total, several hundred individual surgical knots are tied, with about half of the knots being for suturing the above-mentioned tissue parts/components together and the other half for suturing the tissue components into the stent/frame structure. The difficulty here is that if a single knot is placed incorrectly, this immediately leads to rejection of the valve prosthesis and additional costs in the manufacturing method. Furthermore, sutures form mechanical weak points that can potentially lead to failure of the implant—as mentioned at the beginning.

Typically, the manufacturing of a TAVI/TAVR valve starts with the mechanical processing of the tissue (e.g. pericardium), where the required tissue component(s) is/are prepared and cleaned (e.g. from the pericardium). In the subsequent crosslinking method, the tissue is usually placed and/or fixed (e.g., stretched at the edges) on a suitable planar mold (e.g., one or more plates or a plastic frame), and placed in a suitable crosslinking solution (e.g., glutaraldehyde solution including glutaraldehyde oligomers) for several days.

Chemical crosslinking by glutaraldehyde oligomers leads to inter- and intramolecular crosslinking in the collagen, and this is essential to protect the tissue from enzymatic degradation and thus ensure the long-term stability of the implant. In addition, this step forces the tissue into a planar shape, facilitating the laser cutting or a punch-out that typically follows.

In this regard, it should be mentioned in general, and without attachment to this theory, that crosslinking in solutions including glutaraldehyde oligomers typically occurs via a plurality of glutaraldehyde macromolecules present in the solution. Due to the large number of molecular variants present, good crosslinking takes place. The spacing of the binding sites on the collagen fibers involved can therefore vary and yet chemically covalent binding can occur due to the glutaraldehyde oligomers.

The background to the need for chemical crosslinking is that biological tissue, unless it is supplied by cells and endogenous methods in the body, is subject to natural decomposition and denaturation methods. Accordingly, it must be selectively processed for further processing into a functional long-term implant.

Glutaraldehyde, more correctly referred to as glutaraldehyde, was first used for chemical fixation in the early 1960s and has since become the gold standard for crosslinking collagen-containing tissues. Chemical crosslinking of the collagen structure by glutaraldehyde reduces the immune response and prevents enzymatic degradation after implantation—without compromising the anatomical integrity of the tissue and the viscoelastic properties of the collagen. In addition to its crosslinking property, it can also be used as a sterilizing agent, as it has a killing effect against bacteria, viruses and spores. The great success of glutaraldehyde is due to its commercial availability at low cost, as well as its excellent solubility and high reactivity.

As exemplified above for TAVI/TAVR valves, artificial compounds of tissues/components (biological and/or artificial), especially tissues for medical use, are known. However, the compounds of the prior art are predominantly made of surgical materials, in particular surgical sutures including one or more surgical knots.

As mentioned, such surgical sutures usually have to be placed manually. This method is very time-consuming, expensive and error-prone—to list just a few of the associated disadvantages. Surgical knots, for example, must be placed individually by personnel in a highly concentrated manner and must always be visually inspected. In addition, each individual knot represents a potential weak point of the medical tissue, since mechanical forces occurring under stress of a medical implant are focused on the knots. Surgical sutures also have a non-negligible space requirement (space requirement), which means that minimum structural sizes of a few millimeters cannot be undercut, especially in the case of medical implants. This noticeably restricts medical implants in their medical fields of application.

The connection of several tissue segments by sutures of surgical material to create a three-dimensional tissue geometry, e.g. of a TAVI/TAVR valve, are known. Furthermore, a method for three-dimensional shaping by rigid shaped bodies on both sides is known, for example, from U.S. Pat. No. 8,136,218 B2. In this method, the tissue is placed between two rigid molded bodies and chemically crosslinked in this state so that the geometry of the molded bodies is permanently imprinted in the tissue.

However, there are also disadvantages associated with the prior art methods. For example, surgical sutures usually have to be placed manually. This method is very time-consuming, expensive and error-prone. The knots must be visually inspected individually. In addition, each individual knot represents a potential weak point, since mechanical forces that occur are focused on the knots. Surgical sutures also have a non-negligible space requirement, which means that minimum structural sizes of a few millimeters cannot be undercut for implants.

Furthermore, the rigid molded bodies described above are not capable of compensating for inhomogeneities in tissue thickness that are naturally always present. In areas of higher tissue thickness, this results in pressure peaks that cause partial fiber compaction and the associated stiffening of the tissue. Visually, these pressure points can be identified as transparent areas on the tissue surface (see FIG. 1; (4), (5)). Air bubbles trapped between the two moldings also have this effect. In addition, usually the rigid molded bodies hinder the access of the crosslinking solution to the tissue, resulting in poorer crosslinking quality of the tissue.

Methods for reducing the thickness of, for example, bovine pericardium by approx. 50% by planar crosslinking between plates are known, for example, from U.S. Pat. No. 7,141,064 B2. Methods for thickness reduction of e.g.

bovine pericardium by layer ablation, e.g. by a laser and subsequent crosslinking under compression in porous ceramic carriers, are known e.g. from US 2013/0310929 A1. Furthermore, methods for three-dimensional shaping by rigid molded bodies on both sides are known, for example, from U.S. Pat. No. 8,136,218 B2. US 2010/0011564 A1 shows a mold assembly for forming a prosthetic valve. EP 3 156 083 A1 describes a method for embossing a 3D mold onto a biological tissue.

In the method described therein, the tissue is placed between two rigid shaped bodies and chemically crosslinked in this state.

The crosslinking of pericardium, e.g. on plastic frames, and a subsequent matching of individual leaflet/skirt components according to their thickness distribution, the tissue thickness profile as well as according to their bending behavior in order to enable a uniform opening and closing behavior of a later TAVI/TAVR valve as an implant is also known.

However, the exemplary methods of the prior art named above are subject to disadvantages. This is due to the fact that the thickness reduction is mostly based on chemical crosslinking under pressure, and thus on the principle of displacement of water from the original tissue, and an associated densification of the fibers of the tissue. However, if the tissue is limited from both sides by a fixed counterform (as, for example, in the case of the use of two rigid molded bodies), there is no sufficient exchange surface for the water, and a very high pressure is necessary to be able to reduce this in turn.

Accordingly, U.S. Pat. No. 7,141,064 B2 specifies a maximum tissue length of 6 inches and a pressure of at least 250 pounds; which, assuming a square maximum area, corresponds to a minimum pressure of 0.5 kg/cm$^2$. However, this high pressing force requires a high technical effort and can lead to damage of the collagen fibers and thus to deteriorated mechanical properties of the resulting tissue. In addition, the thickness reduction that can be achieved with this method is approx. 50%, which, however, does not correspond to the maximum thickness reduction that can be achieved.

The abovementioned removal of layers to reduce the tissue thickness inevitably results in damage to the tissue surface and thus to load-bearing collagen fibers. This in turn entails the risk of inadequate mechanical properties or insufficient long-term performance for the tissue obtained.

The rigid molded bodies mentioned at the beginning are, for example, unable to compensate for the naturally always present inhomogeneity in the tissue thickness. In areas of higher tissue thickness, this also results in pressure peaks which cause partial fiber compaction and the associated stiffening of the tissue. Visually, these pressure points can usually be identified as transparent areas on the tissue surface (see FIG. 1). Air bubbles trapped between the two moldings also cause this effect (see FIG. 1). In addition, the rigid mold bodies hinder the access of the crosslinking solution to the tissue to be formed, which in turn results in poorer crosslinking quality of the tissue.

A current typical method for the fixation of biological tissue for use as a heart valve implant (e.g., a TAVI/TAVR valve), provides for planar crosslinking of the original tissue, e.g., on plastic frames, to achieve wrinkle-free results. After chemical fixation, e.g. using glutaraldehyde solution, the individual tissue components for a TAVI/TAVR valve (e.g. one or more leaflets, one or more skirt elements; inner and/or outer skirt) are e.g. laser cut or via other cutting, and subsequently grouped according to their thickness profile and flexibility or assigned as a suitable match. This is a selection method for finding suitable and matching skirt/leaflet combinations. However, the necessary selection method results in high reject rates; in addition, the flexibility of the tissue is reduced due to the pretension on the frame during crosslinking.

SUMMARY OF THE INVENTION

A preferred method for chemically crosslinking and optionally shaping (including thickness reduction) substantially non-cross-linked tissue, in particular biological tissue, using a permeable material layer. The method can be used in combination with a stepless pressure load/compression on the tissue, so as to always allow fluid transport into and out of the tissue to be treated under the chemical cross-linking; along the lines of drainage. The method can be carried out under different pressure loads/compressions, in particular in order to specifically influence the resulting tissue properties, and, for example, to bring about a homogeneous thickness distribution of the tissue and/or to deliberately and specifically place inhomogeneities, if desired. Furthermore, the method allows the introduction/imprinting of a consistent three-dimensional shape into the tissue to be treated, e.g. of inhomogeneities in the thickness of the tissue.

BRIEF DESCRIPTION OF THE DRAWINGS

Embodiments of the invention and further features and advantages of the invention will be described hereafter based on the figures. In the drawings.

DETAILED DESCRIPTION OF THE PREFERRED EMBODIMENTS

Figure 1:
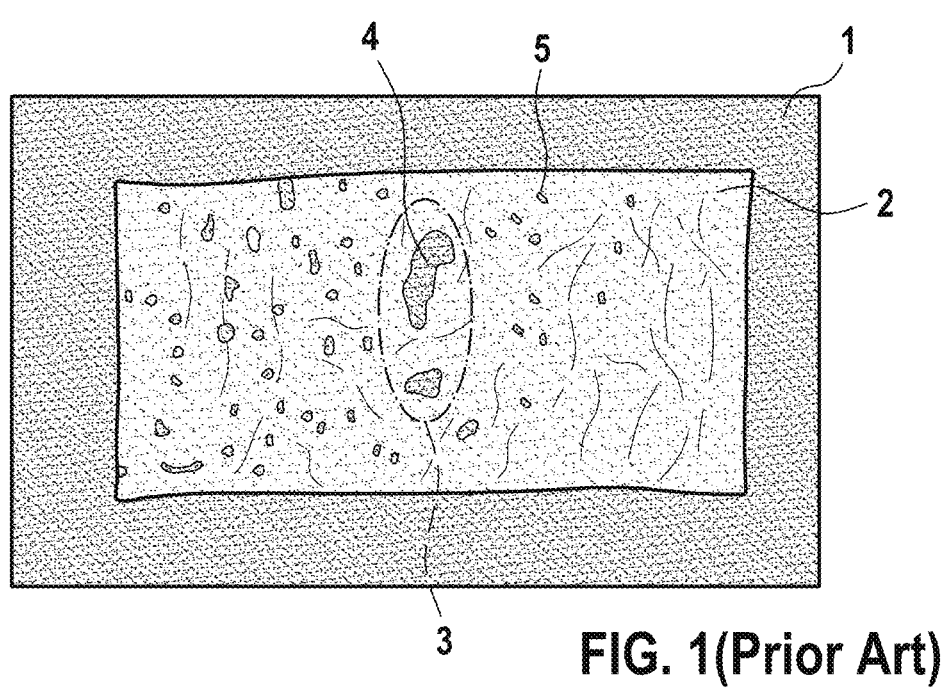
FIG. 1 (Prior Art) shows an example of a typical tissue surface of pericardium on a substrate after chemical cross-linking with glutaraldehyde solution according to the state of the art using rigid moldings on both sides.

With regard to the above-mentioned disadvantages of the prior art, a technical problem is to provide a method for the production of crosslinked and/or shaped tissue, in particular crosslinked and/or shaped biological tissue, in particular for medical applications, which enables targeted adaptation of the tissue properties, such as in particular thickness, shape and/or flexibility, directly during chemical crosslinking. Thus, the method according to the invention is intended to provide, among other things, tissue/tissue components with optimized thickness homogeneity.

The present invention relates to a method for chemically crosslinking and optionally shaping (including thickness reduction) substantially non-crosslinked tissue, in particular biological tissue, using a permeable material layer, optionally in combination with a stepless pressure load/compression on the tissue, so as to always allow fluid transport into and out of the tissue to be treated under the chemical crosslinking; along the lines of drainage. According to the invention, the method can be carried out under different pressure loads/compressions, in particular in order to specifically influence the resulting tissue properties, and, for example, to bring about a homogeneous thickness distribution of the tissue and/or to deliberately and specifically place inhomogeneities, if desired. Furthermore, the method enables the introduction/imprinting of a consistent three-dimensional shape into the tissue to be treated, for example inhomogeneities in the thickness of the tissue, in order to exert a sealing function against a vessel lumen with additional use of a pressure compensation layer and at least one rigid counterform in the method, such as for example a foam layer, in particular a polyurethane foam layer.

The optimized thickness homogeneity is to be understood as significantly better than in conventionally crosslinked tissue. For example, pericardium in conventionally crosslinked tissue shows a variance in thickness homogeneity of e.g. 160-200 µm. In contrast, a pericardium that has undergone a thickness-reducing method according to the invention shows a thickness variance around 40 µm, as a reduced thickness by up to a factor of 5 in section. In this case, a tolerance of +/−5 µm can be specified as the measurement tolerance per measured point.

Due to the controlled and even willingly "adjustable" final thickness of the tissues obtained from the methods disclosed herein, thickness-homogeneous (in particular ultra-compact) tissues/tissue components are provided, which may also allow a more evenly distributed mechanical load absorption.

Consequently, a further object of the present invention is to provide, in particular, methods for the production of ultra-thin or ultra-compact tissue or to provide corresponding tissue components.

In the context of the invention, the terms "ultrathin" and "ultracompact" with reference to tissue denote that the treated tissue has a thickness homogeneity characterized by a substantially constant thickness of the tissue of preferably less than 40% of the thickness of the starting tissue (with a tolerance range for a measurement error of ±5 µm)

Normally, the normal remaining thickness of a pericardial tissue is 120%-40% of the initial thickness. 120%, i.e. even an increase in thickness, for the case of crosslinking performed freely on a mesh (pericardium becomes thicker during free crosslinking with glutaraldehyde). The thickness reduction is already 40% for standard UTT patches. However, anything below this marks extremely thin patches, where 10% of the initial thickness would be an absolute lower limit. The absolute minimum value for porcine pericardial tissue, for example, is 20 µm thickness.

The methods disclosed herein of a deliberately targeted thickness influence/reduction, up to ultra-thin biological tissue, with an optional additional shaping and/or influencing of the flexibility of the tissue, enable new fields of application, in particular new medical fields of application.

The above-mentioned adaptation of the tissue properties, such as in particular the thickness, but at the same time also the shape and/or flexibility, is achieved by chemical crosslinking and optional shaping using a permeable material layer (preferably made of a technical fabric), optionally in combination with a (continuous) pressure load on the tissue and the use of an added pressure compensation layer, such as, for example, a compressible foam that is also permeable, or an elastomer mat/silicone mat that is not permeable. Thus, the pressure compensation layer can be permeable, but it does not have to be. Essential for the access of the crosslinking solution to the tissue and for the drainage of the tissue water is the addition of a permeable material layer, e.g. actually only one, or at least two or even more permeable material layers, preferably made of a technical fabric. The at least one, preferably two, permeable material layer(s) may be an organic polymer layer, preferably a polyester layer. The at least one, preferably two, permeable material layer(s) has a mesh size or pore size enabling the crosslinking solution to pass through the permeable material layer(s). This enables a sufficient contact of the tissue with the crosslinking solution passing through the permeable material layer(s). The at least one, preferably two, permeable material layer(s) can have a mesh size or pore size of less than 60 µm, preferably ranging from 10 µm to 60 µm. Mesh sizes or pore sizes of less than 60 µm lead to even tissue surfaces. Mesh sizes or pore sizes larger than 60 µm lead to uneven tissue surfaces so that an imprinted structure on the surface of the biological tissue may be visible to the naked eye. Nevertheless, mesh sizes or pore sizes larger than 60 µm can be used to imprint structures on the surface of the biological tissue if this is desired, namely, whenever one wishes to imprint a technically functional surface on the tissue to be treated, such as, for example, a roughening of a surface or specific depressions in a surface, etc. The at least one, preferably two, permeable material layer can have a thickness of 40 µm to 70 µm. Preferably the tissue is sandwiched between two permeable material layer(s).

In addition to the at least one, preferably two, material layers at least one pressure compensation layer can be used. The pressure compensation layer, even if it is not permeable, at least supports the adequate distribution of the crosslinking solution by its technical properties. The at least one, preferably two, pressure compensation layer(s) avoid(s) local stress peaks and enable a homogeneous thickness of the obtained tissue. Preferably the tissue is sandwiched between two permeable material layer(s) and the two permeable material layer(s) are sandwiched between two pressure compensation layers and the two pressure compensation layers are sandwiched between two (rigid) counterforms (via which an external pressure is applied). The at least one, preferably two, material layers and/or the at least one pressure compensation layer can be made of a hydrophilic material. Hydrophilic materials enable a better permeability and/or wettability with the crosslinking solution, preferably an aqueous (glutar)aldehyde solution, than hydrophobic materials. The at least one pressure compensation layer can be a solid polymeric foam, preferably a polyurethane foam. The at least one pressure compensation layer can have a compression hardness of 65 kPa or less, preferably 60 kPa, and/or a density of 45 kg/m³ or less, preferably 45 kg/m³. The higher the compression hardness and bulk density are selected the higher is the pressure built up on the tissue.

That is, in some embodiments of the invention, a method is provided which, on the one hand, equalizes the natural inhomogeneity of the tissue, possibly allowing shaping of the tissue to be treated, and, on the other hand, allows access of the crosslinking solution to the tissue to be crosslinked/shaped. This is essentially realized for these embodiments by a stepless pressure load on the tissue to be treated, preferably between two rigid and possibly perforated counterforms, and by one or more pressure compensation layers located in between, such as one or more compressible foams, in addition to the permeable material layer to be used essentially anyway.

In addition, a three-dimensional shape can be introduced/imprinted into the tissue during chemical crosslinking, e.g. by glutaraldehyde, by a combination of shaping of the foam and the counterform(s) that is arbitrarily selected but suitable for the method.

Alternatively, there is another possibility of 3D molding besides the variant with the molded foam: The basic method remains the same, but the foam can be replaced by a silicone mat, but in this case more emphasis must be placed on perforations on the opposite side, i.e. the counterform. That is, the structure would be as follows from bottom to top: i) porous or perforated solid lower counterform, ii) mesh as a technical fabric and thus an example of a permeable material layer, iii) the tissue to be treated, iv) silicone layer as a pressure compensation layer, v) followed by upper solid counterform. The silicone pressure compensation layer can also be, for example, a balloon of silicone used to pressurize the pericardium pneumatically or hydraulically from the inside out against a perforated outer mold. With this 3D arrangement, it is not only possible to create valve segments, but also, for example, a complete valve with an adhesive seam.

As mentioned above, in one embodiment according to the invention, it is essential for chemical crosslinking and simultaneous molding to use a pressure compensation layer, such as a compressible foam or a firmer silicone mat. For the drainage function with respect to the chemical crosslinking solution and the tissue water, however, the only decisive factor is that a permeable material layer of technical fabric, such as a mesh, is present. This allows fluid exchange between the tissue and the environment. This makes it possible to remove the water contained in the tissue by applying comparatively little force and, at the same time, to reduce the tissue thickness considerably (from, for example, 200 μm initial thickness to up to 20 μm final thickness of the treated tissue, i.e. 10% of the initial thickness), while retaining the mechanical stability of the tissue itself. In addition, the permeable pressure compensation layer ensures good contact between the tissue and the crosslinking solution.

The methods of the present invention thus enable a specific adaptation of the properties of biological tissue, in particular collagen-containing biological tissue, such as in particular thickness, shape and flexibility (but not limited in this respect), namely this by a specific adaptation of the chemical crosslinking step of the tissue, whereby on the one hand the tissue waste is reduced and on the other hand new fields of application, in particular new medical fields of application, are opened up by the arbitrary adaptation.

The method is used, for example, to produce ultrathin pericardium, which can be reduced in thickness by about 50% even by applying a low force of 0.1 kg/cm² during fixation. Since mechanical stability is maintained despite the substantial thickness reduction, the tissue is suitable for use as a leaflet/skirt tissue component in a TAVI/TAVR valve, for example. Advantage of using such low force application is on the one hand the simple technical feasibility and on the other hand the low stress on the collagen fibers.

Another major advantage of the methods with the crosslinking variants under infinitely variable pressure is the improved thickness homogeneity with individually adjustable final thickness of the tissue to be treated, in particular non-crosslinked tissue such as collagen-containing biological tissue. Depending on the crosslinking variant, this varies between 120% (see embodiment variant 1—crosslinking without stepless pressure loading; resulting swelling of the tissue) and 40% (see embodiment variant 2—crosslinking under stepless pressure loading and associated thickness reduction) compared to the initial thickness in the native state.

Due to the reduced variation in the thickness of the tissues obtained according to the invention, the scrap within the production can be significantly reduced. The optional additional use of one or more, possibly permeable, pressure compensation layers (such as a compressible foam) for force transmission guarantees the equalization of the thickness differences naturally occurring in the biological tissue—without causing local stress peaks that can lead to local stiffening of the tissue.

A further advantage is that the same components described above can also be used to produce three-dimensional (3D)-shaped tissue, in particular 3D-shaped, collagen-containing biological tissue (see embodiment variant 3—crosslinking under stepless compressive loading and associated thickness reduction in the presence of at least one pre-shaped rigid and optionally perforated counterform).

Furthermore, according to the invention, the methods disclosed herein can also be used to bring about connections/joints of tissue pieces.

Due to the different variants and implementation possibilities of the methods according to the invention, very wide-ranging areas of application result. For example, the cross-linked and optionally formed tissue can be found in a TAVI/TAVR valve (valve component but also inner and/or outer skirt elements to reduce paravalvular leakage; PVL), as a stent-graft, as a pouch for pacemakers or, for example, as a collagen tube, as a Left Atrial Appendage Closure Device, as all four heart valve prostheses, as esophageal implants, as bile duct implants.

The present invention describes, among other things, a method for sutureless and integral connection/jointing of biological tissue for use in a prosthetic aortic valve to be implanted in place of a natural aortic valve.

The tissue according to the invention is to be understood as biological tissue. The biological tissue may be an autologous, xenogeneic or allogeneic tissue. In principle, all types of tissue e.g. from non-mammalian or mammalian tissue including human tissue can be used. The tissue may be derived from pig (porcine tissue), sheep, goat, horse, crocodile, kangaroo, ostrich, monkey, preferably primate, octopus, rabbit or cattle (bovine tissue). Tissue that can be used may be collagen containing tissue, pericardial tissue, skin, ligament, connective tissue, tendons, peritoneal tissue, dura mater, tela submucosa, in particular of the gastrointestinal tract, or pleura. The tissue can be in its native form or in a processed form or can include combinations thereof.

Autologous tissue (in medicine) refers to tissue that was isolated from the human or animal body and is to be re-transplanted elsewhere in the same human or animal body (i.e. originating from the same human or animal body or in other words donor and recipient are the same). The autologous tissue can be in its native form or in a processed form or can include combinations thereof. The autologous tissue to be used includes (chemically and/or biochemically) crosslinkable groups.

Allogeneic tissue (in medicine) refers either to material that was isolated from a(nother) human or animal body that is genetically distinct from the human or animal body, but of the same species. Thus, allogeneic (also denoted as allogenic or allogenous) tissue is tissue that was isolated from a human or animal body which is different from the human or animal body where the implant is to be implanted. Allogeneic tissue can be not from the patient itself (but from a genetic different donor of the same species). Allogeneic here also includes hemiallogeneic (genetically different because of being derived from one parent of the same species and one parent from another species). The allogeneic tissue can be in its native form or in a processed form or can include combinations thereof. The allogenic tissue to be used includes (chemically and/or biochemically) crosslinkable groups.

Xenogeneic tissue (in medicine) refers to tissue that was isolated from a human or animal body of a different (heterologous) species. Thus, xenogeneic (also known as xenogenous or xenogenic) tissue is material that was isolated form a human or animal body which is different from the human or animal body where the implant is to be implanted. Xenogeneic tissue may also refer to tissue based on human or animal donor cells (cells obtained from a or the human or animal donor) being cultivated in a bioreactor or being obtained via 3D printing. The xenogeneic material, e.g. tissue, can be in its native form, in a fixed form, in a processed form or can include combinations thereof.

Tissue is to be understood as biological tissue. Biological tissue preferably has an organizational level intermediate between cells and a complete organ Usually, the initial tissue must be thoroughly cleaned and prepared prior to implantation. As far as possible, the tissue is modified in such a way that it is not recognized by the body as foreign tissue, has as little calcification as possible, and has as long a service life as possible. Essentially, such a method for preparing tissue includes several steps:

One possible preparation step is the so-called decellularization of the tissue. In this step, cell membranes, intracellular proteins, cell nuclei and other cellular components are almost completely removed from the tissue to obtain an approximately pure extracellular matrix. Cells and cellular components remaining in the tissue represent in particular a possible cause of undesired calcification of the biological implant material. Decellularization should be carried out so gently that the structure of the extracellular matrix and in particular the collagen fibers in the extracellular matrix remain as unaffected as possible, while on the other hand all cells and cellular components contained therein are removed from the tissue as completely as possible.

Preferably, according to the invention, the biological and/or artificial tissue is subjected to a pretreatment including an optional decellularization with a suitable detergent, preferably with a solution containing surfactin and deoxycholic acid. The decellularization can also be carried out in another way, for example by lysis of the cells or by osmotic digestion.

In the context of the invention, the expressions/terms "biological(s) and/or artificial(s) tissue" or similar terminology describe the tissue types suitable for the seamless joining/jointing methods according to the invention. That is, for example, (purely) biological tissue is tissue of (purely) natural origin, e.g., porcine pericardium taken from a porcine pericardium. (Purely) artificial tissue is tissue that has been artificially produced, for example, from one or more different polymer(s)—e.g., by suitable 3D printing methods or the like. Biological and artificial tissue refers to mixed forms of e.g. a biological basic substance such as porcine pericardium, but including artificial materials, e.g. for local reinforcement of certain tissue regions, which are exposed to e.g. enormous physiological pressure and/or tensile loads—e.g. leaflets of a TAVI/TAVR valve. However, in the context of the invention, common to all these tissue types, and essential, is that they include crosslinkable groups, e.g. free amino groups, in particular collagen fibers, which are (chemically and/or biochemically) crosslinkable.

Figure 2:
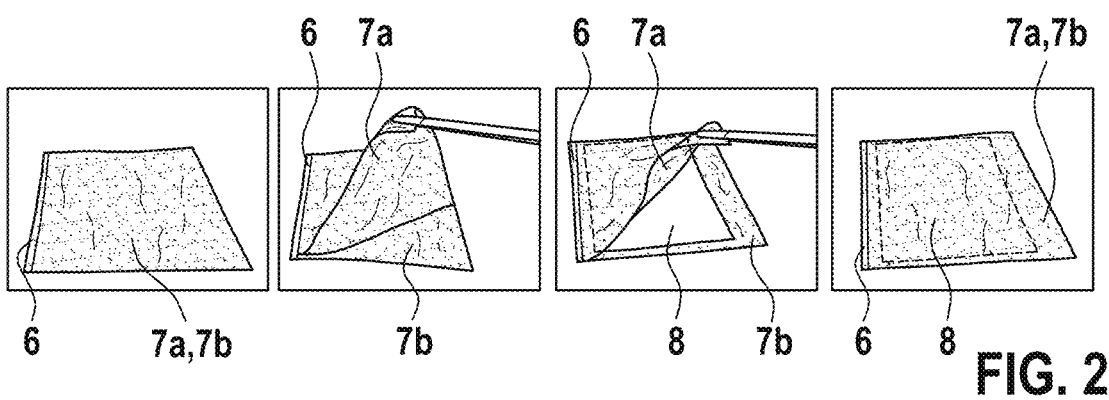
FIG. 2 shows a first exemplary embodiment of the method according to the invention with (purely) planar chemical crosslinking of pericardial tissue—without pressure load.

It is also essential for the methods according to the invention that the starting tissue/components are introduced into the methods according to the invention essentially non-crosslinked at least in the overlap region (i.e. the tissue region(s) to be joined/joined; see, for example, (3) in FIGS. 1 and (6) in FIG. 2), but preferably in its entirety; i.e. that, if possible, no substantial pre-crosslinking has taken place, for example by glutaraldehyde solution. Substantially non-crosslinked with respect to tissue throughout the application means that the tissue includes (chemically and/or biochemically) crosslinkable groups, preferably more than 50% (chemically and/or biochemically) crosslinkable groups. This means that the proportion of crosslinkable groups in the tissue to be treated is greater than 50%, preferably greater than 60%, even more preferably greater than 80%, most preferably greater than 90%. However, this also means that lightly or only slightly pre-crosslinked or partially crosslinked tissue is suitable for the methods of the present invention.

The methods according to the present invention are thus suitable for seamless joining/joining of substantially non-crosslinked tissue, native tissue, non-crosslinked decellularized tissue or non-crosslinked non-decellularized tissue. Also suitable are natively dried tissues, which optionally have also been previously subjected to decellularization. The prerequisite is always that the tissue to be joined/joined must contain crosslinkable groups, e.g. free amino groups, in particular collagen, e.g. contained in collagen fibers.

Furthermore, on the method side, the present invention includes a chemical crosslinking of tissue joining partners including crosslinkable groups, such as, for example, free amino groups, by a suitable crosslinking agent under static, quasi-static or periodic pulsatile pressure loading in a defined overlap region for seamless, dense and tight tissue closure disclosed—for example, for tissue closure for a one-piece valve component made of pericardial tissue for a TAVI/TAVR valve. Thereby, a seamless, homogeneous, and at the same time mechanically stable connection/jointing of tissue/tissue components is achieved.

That is, the invention exploits, among other things, for the first time in a targeted manner, in sufficient quantity and density, the effect that a crosslinking agent such as, for example, glutaraldehyde can also form interfibrillar connections/crosslinks between two joining partners, such as, for example, tissue surfaces for a one-piece valve component, in order to realize a seamless, materially bonded and durable connection/joint.

The crosslinking agent is preferably an aldehyde-containing crosslinking agent, more preferably glutaraldehyde. In alternative embodiments of the invention, the crosslinking agent contains carbodiimide, formaldehyde, glutaraldehyde acetals, acyl azides, cyanimide, genepin, tannin, pentagalloyl glucose, phytate, proanthocyanidin, reuterin and/or epoxy compounds.

An exemplary and preferred crosslinking agent is a glutaraldehyde-containing solution consisting of glutaraldehyde at a concentration of 6 g/l in DPBS without calcium and magnesium.

Glutaraldehyde, e.g. in aqueous solution, is a known crosslinking agent, especially of free amino groups, proteins, enzymes, and e.g. collagen fibers (Isabelle Migneault, Catherine Dartiguenave, Michel J. Bertrand, and Karen C. Waldron: *Glutaraldehyde: behavior in aqueous solution, reaction with proteins, and application to enzyme crosslinking; BioTechniques* 37:790-802 (November 2004).

A particular advantage of the methods disclosed herein is that, for example, a glutaraldehyde solution can in principle be used as a crosslinking agent irrespective of concentration.

In one embodiment, for example, the tissue/components to be bonded is placed in a glutaraldehyde oligomer-containing solution at pH 7.4 for 48 hours at a temperature of 4° C. during the chemical crosslinking step, and subjected to quasi-static or periodic pulsatile pressure loading/compression.

In general, the skilled person is aware that chemical crosslinking, depending on the tissue to be treated and the desired properties of the crosslinked tissue, can also be regulated or controlled by temperature. Crosslinking generally starts at a temperature above 0° C. Preferred temperature ranges for chemical crosslinking in the sense of the invention are 1-50° C., preferably 10-50° C., more preferably 20-50° C., even more preferably 25-40° C., most preferably 35-40° C., for example at 37° C.

Advantageously, the tissue is rinsed at least once, preferably several times, with a suitable solvent, in particular a buffered salt solution and/or an alcohol solution, before and particularly preferably after the decellularization (if it is decellularized tissue). Buffered sodium chloride solutions and/or an ethanol solution are particularly advantageous.

In one embodiment of the present invention, alpha-gal epitopes may additionally be removed from the tissue in a further treatment step, which may be performed after or before the optional decellularization step. Any suitable alpha-galactosidase can be used for such an additional treatment step, e.g., alpha-galactosidase from green coffee bean (GCB) or *Cucumis melo.*

As mentioned above, on the device side, the problem posed is solved, inter alia, by a medical implant including the seamlessly and integrally bonded/joined tissue subjected to one of the methods according to the invention.

With the context of the present invention, the term "medical implant" or similar terms particularly includes stent-based implants and heart valve prostheses, particularly aortic valve prostheses, which are stent-based. According to the invention, the term "medical implant" also reads to any medical implant for which the suture-free joined/connected tissue is suitable as a method product, for example, to seal the implant against an anatomical structure.

Also included as a medical implant are pockets that can receive and be implanted with, for example, a pacemaker, an implantable leadless pacemaker, or a defibrillator.

Nowadays, stents are particularly frequently used as implants for the treatment of stenoses (narrowing of blood vessels). They have a body in the form of a possibly perforated tubular or hollow cylindrical basic structure, which is open at both longitudinal ends. The basic structure of the stent may be composed of individual meshes formed by zigzag or meander-shaped webs. The tubular basic structure of such an endoprosthesis is inserted into the vessel to be treated and serves to support the vessel.

Stents have become particularly popular for the treatment of vascular diseases. The use of stents can widen constricted areas in the vessels, resulting in a gain in lumen. Although the use of stents or other implants can achieve an optimal vessel cross-section, which is primarily necessary for the success of the therapy, the permanent presence of such a foreign body initiates a cascade of microbiological methods which, for example, promote inflammation of the treated vessel or necrotic vascular changes and which can lead to a gradual overgrowth of the stent through the formation of plaques.

Stent graft(s)" are stents that contain a fleece or other flat covering, such as a film or tissue, on or in their often grid-like basic structure. In this context, the term "nonwoven" is understood to mean a textile tissue formed by individual fibers.

In the context of the present invention, the term "nonwoven" also includes the case in which the textile sheet-like structure consists of only a single "continuous" fiber. Such a stent graft is used, for example, to support weak points in arteries, esophagus or bile ducts, for example in the area of an aneurysm or a rupture of the vessel wall (so-called bail-out device), in particular as an emergency stent.

Medical endoprostheses or implants for a wide variety of applications are known in great variety from the prior art and can be combined with the seamless and materially joined tissue of the invention for suitable purposes. Implants in the sense of the present invention are in particular endovascular prostheses or other endoprostheses, e.g. stents (drug eluting stents, bile duct stents, vascular stents, peripheral stents or, e.g., mitral stents), endoprostheses for closing persistent foramen ovale (PFO), pulmonary valve stents, endoprostheses for closing an ASD (atrial septal defect), as well as prostheses in the area of hard and soft tissue. Also possible as an implant is a left atrial appendage closure device (LAAC).

In an alternative, preferably the medical implant is a prosthetic heart valve, more preferably a TAVI/TAVR valve, which includes an artificial heart valve made of sutureless and materially bonded/joined tissue and/or a seal made of said tissue attached, preferably sutured, to an expandable or self-expanding and catheter implantable base frame, stent, or retaining device.

In all embodiments of the present invention, the decellularization method, if performed, is applied to tissue that is not conventionally crosslinked after decellularization; rather, crosslinking occurs exclusively in the methods disclosed herein under quasi-static or periodic pulsatile pressure/compression in one or more selected overlap region(s) of the tissues involved.

Such a tissue could be used, for example, in cases where cellular ingrowth is preferred, such as in the treatment of a wound or burn with a porous matrix or when used as a means of sealing an implant or graft.

After the optional decellularization and crosslinking methods disclosed herein, the tissue/tissue component can undergo a dimensional and structural stabilization step. It has also been shown that stabilization of the tissue can be significantly enhanced by exposure to certain stabilizing agents.

In a preferred stabilization step, the tissue is exposed to at least one solution containing glycerol and/or polyethylene glycol, wherein the tissue is exposed to either one of these solutions or to the two solutions sequentially in any order and composition as first and second solutions or to both solutions or even to multiple solutions with different molecular weights of PEG simultaneously as a mixture of solutions or sequentially in any order. When drying tissue, e.g., for storage or transportation of the tissue, the stabilization method is preferably carried out prior to drying.

As a non-limiting example, the stabilization method may be performed, for example, after decellularization and crosslinking by immersing the tissue in a series of one or more stabilizing solutions of glycerol and/or polyethylene glycol to sufficiently saturate the tissue with stabilizing agents, and ultimately to produce a stable, dry tissue with a seamless joint/joint. Saturation times can vary, but typically take about 5 minutes to 2 hours or 5 minutes to 15 minutes, depending on the properties of the tissue. The stabilized tissue can be dried by placing the tissue, for example, in a suitable environment with constant low relative humidity or, for example, controllable humidity and/or temperature, for example, in a climate chamber or desiccator and reducing the relative humidity. For example, from 95% to 10% over 12 hours at 37° C. It is obvious to the person skilled in the art that, depending on the circumstances, another suitable drying protocol may be applied.

In general, it is true for the entire present disclosure that the skilled person can suitably adjust the technical parameters such as times, amounts, concentrations, temperatures and, for example, pressures depending on the type of tissue to be treated and the desired crosslinking/bonding results.

The polyethylene glycol-containing solutions typically contain polyethylene glycol with an average molecular weight between 150 g/mol and 6000 g/mol, or a mixture thereof. As used herein, the term "between" also includes the upper and lower specified values. Thus, an average molecular weight between 150 g/mol and 6000 g/mol is intended to include 150 g/mol and 6000 g/mol.

In some embodiments, at least one polyethylene glycol-containing solution includes polyethylene glycol having an average molecular weight between 150 g/mol and 200 g/mol, between 150 g/mol and 300 g/mol, between 200 g/mol and 300 g/mol, between 200 g/mol and 600 g/mol, between 200 g/mol and 400 g/mol, between 150 g/mol and 400 g/mol, or between 400 g/mol and 600 g/mol. According to a particularly preferred embodiment, the polyethylene glycol-containing solution provided alone or before or after a glycerol solution contains polyethylene glycol at or about 150 g/mol to 300 g/mol or at or about 200 g/mol (e.g., PEG200), and in an even more preferred embodiment, the polyethylene glycol-containing solution contains 40% PEG200 or about 40% PEG200.

The term "about" as used herein is intended to encompass a variation above and below the stated amount that would be expected in normal use, such as a variation of 5% or 10%.

Glycerin may be added to any of the above stabilizing solutions to form a mixture, or it may be provided separately for stabilizing purposes, such as in aqueous solution.

In some embodiments, a subsequently applied polyethylene glycol-containing solution contains polyethylene glycol having a higher average molecular weight than a previously applied polyethylene glycol-containing solution. In some embodiments, the subsequently applied polyethylene glycol-containing solution contains polyethylene glycol having an average molecular weight between 200 g/mol and 6000 g/mol, or a mixture thereof. In some embodiments, the subsequently applied polyethylene glycol-containing solution includes polyethylene glycol having an average molecular weight between 300 g/mol and 1500 g/mol, or a mixture thereof.

In some embodiments, the subsequently applied polyethylene glycol-containing solution includes polyethylene glycol having an average molecular weight between 400 g/mol and 1200 g/mol, or a mixture thereof. In some embodiments, the subsequently applied polyethylene glycol-containing solution includes polyethylene glycol having an average molecular weight between 400 g/mol and 800 g/mol, or a mixture thereof. In some embodiments, the subsequently applied polyethylene glycol-containing solution includes polyethylene glycol having an average molecular weight between 400 g/mol and 600 g/mol, or a mixture thereof. In some embodiments, the subsequently applied polyethylene glycol-containing solution contains polyethylene glycol having an average molecular weight of 400 g/mol (PEG400) or about 400 g/mol.

Again, glycerol may be added to any of the above stabilizing solutions to form a mixture, or it may be provided separately as a stabilizing solution.

In this regard, the skilled person is aware that the temperature during the stabilization step can affect the results. For example, too high a temperature (e.g., above about 85° C.) will cause denaturation and irreversible damage to the tissue cross-linked, e.g., glutaraldehyde cross-linked, for the purpose of bonding/jointing. Again, however, too low a temperature can lead to a solution that is too viscous. Preferably, exposure to the stabilizing solutions is at 37° C., but temperatures from room temperature up to 60° C. should be tolerable.

As mentioned at the outset, the methods described in the present invention are suitable for the preparation of essentially non-crosslinked tissue or, for example, decellularized, essentially non-crosslinked tissue—with the proviso that crosslinkable groups, e.g., free amino groups, must be present in the tissue. Optionally, all of the tissues addressed within the scope of the invention may be stabilized as described herein. Optionally, alpha-gal epitopes can be removed from all these tissues by a suitable alpha-galactosidase treatment (preferably originating from GCB or *Cucumis melo*, see above).

With regard to the implant itself, the aforementioned problem is further solved by an implant containing biological tissue which has been subjected to one of the methods according to the invention and, if necessary, subsequently stabilized and/or dried.

In this case, the drying of the tissue is designed in such a way that a slow and gentle removal of the water in the liquid state from the tissue is ensured. This is advantageously achieved by the controlled reduction of the ambient humidity of the biological tissue in a suitable environment, such as a desiccator or a climatic chamber, with controlled adjustment of the parameters of the ambient atmosphere of the biological tissue.

A core of the method for seamless joining according to the invention lies in the surprising realization that various suitable crosslinking agents, such as for example and preferably glutaraldehyde, not only have the ability to form inter- and intramolecular crosslinks within a collagen fiber (see prior art above), but also interfibrillar crosslinks between individual fibers. Thus, it is possible for the first time to generate seamless and materially cohesive connections/joints in an overlapping area of two tissue joining partners, which include cross-linkable groups, such as free amino groups, e.g. containing collagen, by simultaneously applying a static, quasi-static or periodic pulsatile pressure load/compression by a suitable device.

The basic requirement for this is that the distance between the collagen fibers is smaller than the length of the cross-linking molecules involved, such as the glutaraldehyde oligomers mentioned above, which form the actual cross-links. Therefore, in the context of the invention, a pressure-generating device has been provided to generate a quasi-static or a periodic pulsatile vertical force application (pressure load/compression), with desired repetition cycles and over a desired time period, to a defined tissue region during the crosslinking method. According to the invention, the pressure generating device can be based on the physical principles of pneumatics, mechanics, and, for example, hydraulics, but is not limited in this respect. In the context of the invention, hydraulics is a particularly preferred embodiment for generating the pressure load/compression.

The basic requirement for said formation of interfibrillar crosslinks is that the distance between the collagen fibers and microfibrils involved is smaller than the length of the glutaraldehyde oligomers involved (see above), which essentially form the crosslink. Appropriate pressing parameters over suitable time periods to reduce the fiber spacing are thus essential to enable a stable, seamless and cohesive bond using glutaraldehyde oligomers. At the same time, however, a high pressing pressure potentially, and thus not necessarily, results in preventing accessibility of the crosslinking solution to the tissue during force application.

Therefore, according to the invention, in a preferred embodiment, not only a quasi-static pressure on the tissue over a suitable longer period of time during crosslinking is considered (quasi-static refers to a constant pressure over a longer period of time (e.g. 300 seconds), which may be less frequently interrupted by short and suitable pressure pauses (e.g. 1 or 2 second(s)), but a periodic-pulsatile pressure load/compression over suitable shorter periods, but with possibly more frequent repetition of the pressure phases, also interrupted by short pressure pauses (e.g. 30 seconds pressure, 1 or 2 second(s) pressure pause, followed by 30 seconds pressure, 1 or 2 second(s) pause, etc.).

That is, in the pressureless phases (pressure pauses) during the crosslinking method, sufficient contact between the crosslinking agent, e.g. the glutaraldehyde oligomers, and the tissue to be joined/joined is ensured in this way. For this purpose, a suitable device is provided with which both a quasi-static, relatively constant pressure can be realized over longer period cycles, and a dynamic, periodic pulsatile pressure can be generated on the tissue, but over shorter and more frequent period cycles.

In an alternative embodiment, it is possible to achieve the crosslinking according to the invention for seamless and material-locking connection/jointing via a static, i.e. permanent pressure, without pauses. The prerequisite for this is to provide a support surface for the tissue to be joined/joined which is perforated, i.e. is open to the crosslinking solution, in order to ensure its access to the tissue to be crosslinked.

The terms "amino group-containing(s)"/"including free amino groups" or similar terminology mean, in the context of the present invention, that the tissue(s) to be joined/joined must include free amino groups that are chemically cross-linkable by a suitable crosslinking agent in order to be seamlessly and cohesively joined/joined via the methods described herein.

A preferred embodiment for amino group-containing tissue(s) are collagen-containing tissues such as connective tissue, skin, subcutaneous tissue, ligaments, cartilage, bone, tendons, teeth, and in particular pericardium (porcine and bovine for example), etc. Accordingly, the methods disclosed herein lend themselves particularly to the production of medical implants in the areas of: Skin, wound healing, therapies of burn patients, replacement of ligaments, cartilage, bone, or tendons, and in implantology. It is clear to the skilled person that due to the very broad medical application possibilities of compounds/joints of e.g. collagen-containing biological tissues, the aforementioned listing is by no means to be interpreted as exhaustive.

With this context, the term "collagen-containing(s)" or similar terms used in the context of the invention describes that the tissue(s) to be joined/joined must include free collagen fibers in order to be seamlessly and cohesively joined/joined via the methods described herein.

Suitable collagen-containing tissues within the scope of the invention are, for example, native collagen-containing tissues, moist collagen-containing tissues, already processed (but essentially non-crosslinked) collagen-containing tissues, such as, for example, already stabilized collagen-containing tissues, already preserved collagen-containing tissues, already dried (non-crosslinked) collagen-containing tissues, already decellularized tissues, as well as mixed forms of the aforementioned tissues.

It is clear to the person skilled in the art that this list of suitable collagen-containing tissue forms is not exhaustive, but that further collagen-containing tissue types may be suitable for the disclosed method.

In accordance with the invention, bonding methods for stabilized, dried (non-crosslinked) tissue in particular have been tested.

In one alternative, even the seamless and material-locking bonding of already fully or partially crosslinked tissue is possible in principle, whereby exceptionally either no crosslinking solution such as, for example, glutaraldehyde solution or only a very low-concentration glutaraldehyde solution (0-1% glutaraldehyde) is additionally required.

In a further preferred variant, the medical implant is a vascular valve prosthesis, in particular a heart valve prosthesis. For example, an aortic valve prosthesis, a tricuspid valve prosthesis, a mitral valve prosthesis and a pulmonary valve prosthesis are suitable examples of a heart valve prosthesis. Typically, such prostheses or implants have a stent-like structure that carries a valve assembly inside it to replace a natural vascular or heart valve. In this regard, the seamless and materially bonded/joined tissue may be applied to a surface of the prosthetic heart valve (internal and/or external).

In a further variant, the medical implant is a dry-stored and/or dry-delivered complete system, in particular a dry-stored/dry-delivered heart valve prosthesis, in particular an aortic valve prosthesis.

In a further variant, the heart valve prosthesis, in particular aortic valve prosthesis, including one or more of the seamless and integral tissue/joint tissue components, is loaded in a dehydrated state into a so-called catheter delivery system and is delivered in this preloaded state to an operating room.

With the context of the invention, the terms/expressions "quasi-static compressive loading/compression" or similar terms/expressions denote an essentially vertical physical application of force to the tissue to be joined/joined, carried out in such a way that it can be considered exclusively as a sequence of equilibrium states. Thus, the time scale on which a quasi-static method occurs must be much slower than the time period in which equilibrium is reached (the so-called relaxation time). Although a respective state of equilibrium prevails to a large extent at each point in time of the method, it is nevertheless generally an objective of the method to obtain different states or a characteristic curve. This means that the equilibrium state at time t1 (pressure load) may well differ considerably from the equilibrium state at time t2 (pressure relief or pressure pause). The above definition is merely intended to exclude the possibility that dynamic or more dynamic methods, e.g. a periodic pulsatile pressure load/compression, have any appreciable influence on the joining/joining behavior of the tissue components to be joined/joined.

Specifically, in the context of the invention, this means that the relationship between "with pressure loading" and "pressure relief/pressure pause" during the chemical cross-linking method in the case of "quasi-static", is more protracted over time for the pressure loading, and with longer periods of time, possibly several times alternating, than in the direct The "periodic-pulsatile" relationship of "pressure load" and "pressure relief/pressure pause" is shorter for the pressure load, which means that the two states "with pressure"/"without pressure" are also shorter over time and, if necessary, are repeated alternately much more often.

Conversely, the terms/expressions "periodic-pulsatile pressure loading/compression" or similar terms/expressions denote that the relationship between "pressure loading" and "pressure relief/pressure pause" during the chemical cross-linking method is more short-lived over time, especially for the pressure loading, and thus the states "with pressure"/ "without pressure" and with smaller time spans also alternate noticeably more often, in direct comparison to the "quasi-static" conditions described above.

Specifically, in the context of the invention, the terms/ expressions "quasi-static pressure load compression" or similar terms/expressions can be used over a ratio of, for example, 300:1 seconds with respect to "with pressure load" (300 seconds) vs. "pressure release/pressure pause" (for example 1 or 2 second(s)), and thus differ from the terms/ expressions "periodic-pulsatile pressure load/compression" or similar terms/expressions in such a way that in the latter case a ratio of e.g. 30:1 seconds exists with respect to "with pressure load" (e.g. 30 seconds) versus "pressure relief/ pressure pause" (e.g. 1 or 2 second(s)).

That is, "quasi-static" includes, for example, a single, constant pressure load/compression on the tissue to be joined/joined of 5 minutes (=300 seconds) in the presence of a suitable crosslinker solution with, for example, 1 or 2 second(s) pressure relief/pressure pause. Likewise, however, "quasi-static" also describes those cases in which two or more times of constant pressure load/compression with the pressure releases/pressure pauses as described above act on the tissue to be joined/joined. That is, even corresponding multiple cycles of this rather protracted "quasi-static" form of pressure loading and very short pressure pauses in between falls under these terms.

In contrast, this means, for example, that "periodic-pulsatile" includes at least two, but also several, short pressure loads/compressions on the tissue to be joined/ joined of, for example, 30 seconds in the presence of a suitable crosslinking solution, but also always with 1 or 2 second(s) pressure relief/pressure pause. This means that even correspondingly multiple cycles of this rather short "periodic-pulsatile" form of pressure loading with short pressure pauses in between fall under these latter terms.

Artisans will appreciated that it is not necessary to slavishly adhere to the exact ratios of 300:1 seconds for "pressure load" (300 seconds) versus "pressure relief/pressure pause" (e.g. 1 second) in terms of "quasi-static", and 30:1 for "pressure load" (e.g. 30 seconds) versus "pressure relief" (e.g. 1 second) in terms of "periodic-pulsatile". 1 second) in terms of "periodic-pulsatile", but rather the relations of the mentioned time spans to each other distinguish the variants "quasi-static" from "periodic-pulsatile" during chemical crosslinking, and the exact values may suitably deviate from the above examples. For example, for "quasi-static" the above-described ratios of 250:1 seconds or, for example, 350:1 seconds are also conceivable, and with regard to "periodic-pulsatile", for example, 15:1 seconds or 30:2 seconds are conceivable.

In the pressureless phases, quasi in the pauses of the external pressure load, a sufficient contact between the chemical crosslinking agent (e.g. glutaraldehyde) and the tissue components in the contact area is ensured in this way.

The above-mentioned alternative case of static crosslinking—without pressure pause—but with a perforated/holed counterform for accessibility of the crosslinking solution is appropriately delimited with the above definition of the quasi-static case.

The person skilled in the art is generally aware that the above-mentioned times can vary considerably depending on the tissue to be treated and the crosslinking agent to be used. Too short times are likely to lead to insufficient stability, too long times are likely to end in a waste of time, and the skilled person would optimize the parameters (time, temperature, concentrations, etc.) depending on the material.

At this point, the overlap length of the tissue components, the physical compression type (hydraulic, mechanical, etc.), cylinder force and the crosslinking time itself should be highlighted as other significant factors influencing the methods according to the invention. Thus, despite a lower breaking load, a reduction in the overlap length tends to result in a higher bond strength. In order to ensure the accessibility of the crosslinking agent, e.g. the glutaraldehyde solution, to the overlap area, a quasi-static or periodic pulsatile pressure load/compression is indispensable according to the invention.

The cylinder force has to be chosen appropriately, depending on the compression area, in order to cause significant (collagen) fiber densification.

With regard to the crosslinking duration, a total period of static, quasi-static or periodic pulsatile compressive loading/ compression of three days is particularly preferred.

The crosslinking of overlapping tissue joining partners according to the invention is a valid concept for the seamless and material-locking joining/joining of tissue, in particular tissue containing collagen. With regard to the application itself, however, the skilled person must always take into account the load limits of the bonded joint in different load cases as well as the effects of the compression method on the properties of the tissue joining partners.

EXAMPLES

The method according to the invention is suitable in principle for chemically/biochemically crosslinkable tissue which is itself essentially non-crosslinked, in particular for essentially non-crosslinked tissue containing collagen. That is, the tissue to be crosslinked according to the invention must have crosslinkable chemical/biochemical groups, such as free amino groups.

The following preferred example is explained using pericardial tissue as an example. Suitable pericardium is that of pigs or cattle in the native, native-stabilized dried or decellularized state, but always non-crosslinked. It is obvious to the person skilled in the art that the methods according to the invention can be used in a generalized manner for tissues, in particular biological tissues, which are essentially non-crosslinked but can be (chemically and/or biochemically) crosslinked.

Common to all embodiments is a processing of the pericardial tissue including both an initial mechanical preparation and the necessary step of chemical crosslinking. The tissue obtained according to the invention can then be subjected to further processing steps, such as stabilization and drying from U.S. Pat. No. 10,390,946 B2.

The methods according to the invention can generally be divided into three variants, which are specifically detailed below—with reference to the figures and reference signs where useful. Common to all variants is the use of at least one permeable material layer (7a, 7b, 7c), e.g. of technical fabric, as a direct support for the pericardial tissue with fluid exchange function; partly in the sense of a drainage of tissue water and for the accessibility of the glutaraldehyde.

Variant 1—Planar Crosslinking with Permeable Material Layers (7a, 7b, 7c)—without Pressure Loading To ensure wrinkle-free crosslinking of pericardial tissue, the pericardium has so far typically been stretched on a plastic frame and then chemically crosslinked, e.g. using a glutaraldehyde solution.

However, since the pericardium is subject to pretension during crosslinking according to this state of the art, the result is a stiffer tissue compared to the initial state. The collagen fibers are therefore no longer present in their original wave form, but are already in a stretched and thus strained state. Various approaches (e.g. spray fixation or fixation on plates) have already been tested, but all these prior art approaches also exhibit the technical disadvantages mentioned at the beginning.

In contrast, the use of at least one permeable material layer (7a, 7b, 7c) disclosed herein, e.g., made of a technical fabric, enables wrinkle-free crosslinking—without biasing/stressing the collagen fibers, so that a significantly more flexible pericardial tissue (8) can be provided for medical applications in particular.

For this purpose, according to the present embodiment example, pericardial tissue (8) is placed (7a, 7b, c) on or between the technical tissue as a permeable material layer after mechanical preparation (e.g. removal of excess tissue, in particular fatty tissue, and cutting) and chemically crosslinked in this state in a 0.5% glutaraldehyde solution (see FIGS. 2, 3, 4, 5). A flexible and wrinkle-free crosslinked pericardium (8) results directly from this method, which, however, still exhibits the original thickness distribution inherent to the biological starting material. In this variant, the technical fabric serves as a permeable material layer (7a, 7b, 7c), but not primarily for a two-dimensional water drainage option in the sense of drainage, but rather for shape stabilization and thus for wrinkle-free crosslinking with simultaneous accessibility of the crosslinking solution.

Various embodiments of this form of crosslinking according to the invention—without the effect of pressure—can be seen in the figures in FIGS. 2, 3, 4 and 5. Specifically, at least two layers (7a, 7b, 7c) of the technical tissue are formed into a kind of receiving pocket (7a, 7b, 7c) for crosslinking, which can receive the previously processed pericardial tissue (8). Several permeable material layers, e.g. of technical tissue, e.g. three, four, five, six or more, can also be arranged and connected (6) on top of each other in such a way that two adjacent layers (7a, 7b, 7c) each form a type of receiving pocket for a pericardial tissue (8). This arrangement of permeable material layers, quasi as a crosslinking unit, is then transferred into a suitable container/receptacle filled with, for example, 0.5% glutaraldehyde solution or alternatively laid out flat/planar in a container/receptacle in such a way that the arrangement of permeable material layers is completely covered with crosslinking solution.

Figure 6:
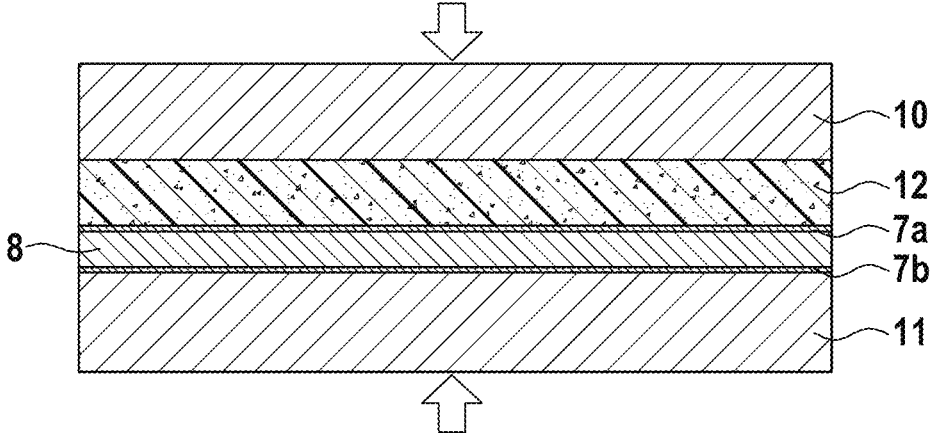
FIG. 6 shows in schematic cross-section the structure/arrangement of various material layers in a device/crosslinking unit suitable for methods of the invention with pressure loading.

Variant 2—Planar Crosslinking with Permeable Material Layers (7a, 7b) Under Stepless Pressure Loading Essential for these embodiments of the method according to the invention is the modification of the chemical crosslinking step. As can be seen in FIG. 6, the crosslinking of the pericardial tissue (8) takes place while it lies in a device or crosslinking unit consisting of two rigid counterforms (10, 11), a polyurethane foam as a pressure compensation layer (12) and two permeable material layers of technical tissue (7a, 7b; in the sense of a drainage). For crosslinking, the entire device is located in a suitable container (e.g. vertical or horizontal) filled with e.g. 0.5% glutaraldehyde solution, so that the device according to FIG. 6 is completely covered by the crosslinking solution.

The use of permeable material layers made of technical fabric (7a, 7b) is essential for successful implementation. On the one hand, this enables water present in the pericardial tissue (8) to be removed with comparatively low pressure, and on the other hand it ensures sufficient accessibility of the crosslinking solution to the tissue.

The compression of the pressure compensation layer (12) under the effect of pressure (see the schematic arrows in FIG. 6) between the rigid counterforms, results in a pressure load on the pericardial tissue (8). The water present in the pericardial tissue (8) escapes via the layers of the technical fabric (7a, 7b) already during the assembly of the device/crosslinking unit. Since the entire device/crosslinking unit is placed in a container filled with, for example, a 0.5% glutaraldehyde solution directly after assembly, which in particular forms interfibrillar crosslinks, the compacted state of the pericardial tissue (8) is permanently maintained. Depending on the applied pressure load, thickness-reduced to ultrathin tissues can be obtained according to the invention, in particular ultrathin porcine pericardium with a final thickness of up to a maximum of 20 μm.

Figure 7A:
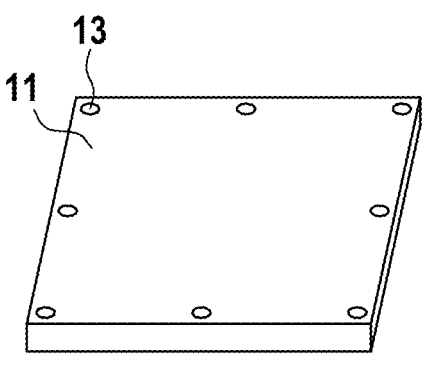
FIG. 7A-H schematically show the individual method steps for setting up the device/crosslinking unit described in FIG. 6 for producing a planar, e.g. ultra-compact pericardial tissue.
Figure 7B:
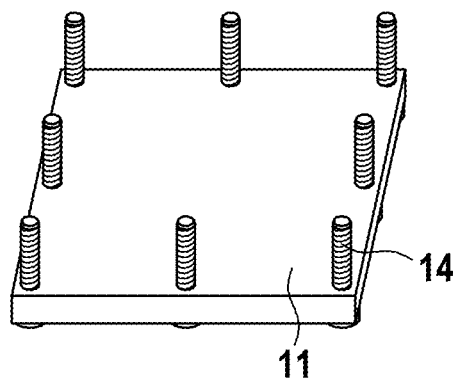
Figure 7C:
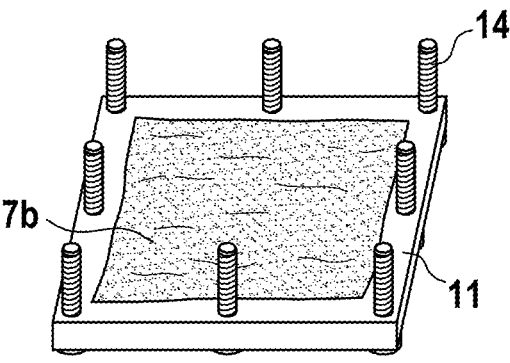
Figure 7D:
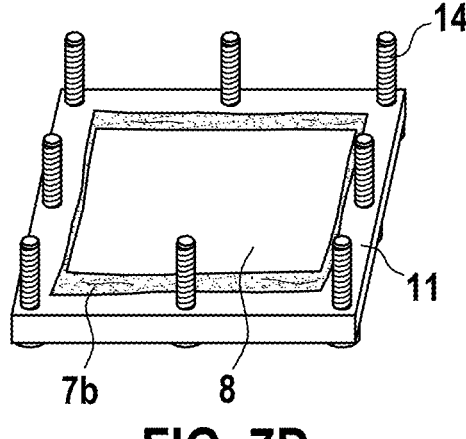
Figure 7E:
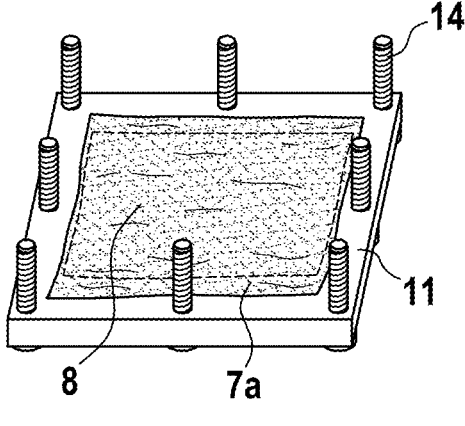
Figure 7F:
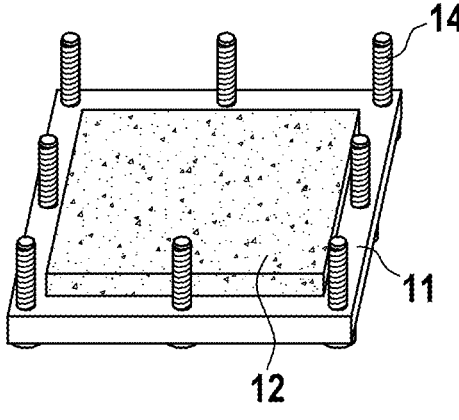
Figure 7G:
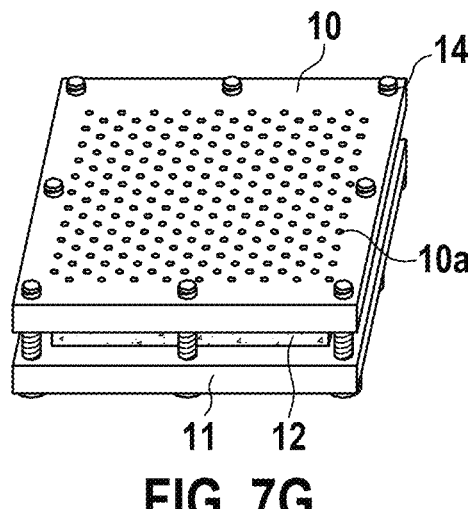
Figure 7H:
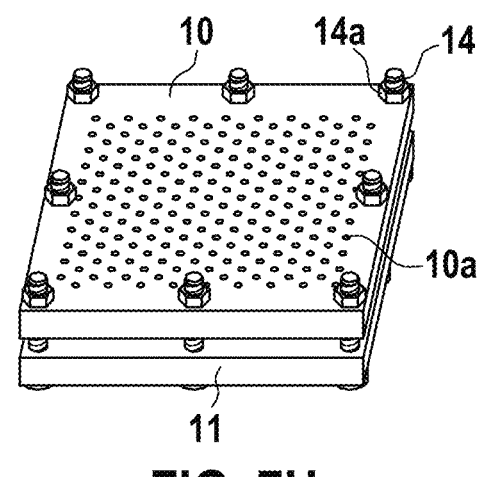

The individual method steps for producing such a planar, ultra-compact/ultra-thin porcine pericardial tissue can be summarized as follows and are explained in more detail with reference to FIGS. 7A-7H:

i) A pericardium, e.g. from a pig, is freshly collected at the slaughterhouse and stored for 2 h at 4° C. in a suitable storage solution, e.g. EDTA/isopropanol or saline;

(ii) The pericardial tissue is rinsed three times for 5 min in saline (0.9%);

(iii) The pericardial tissue is prepared wet in saline (0.9%): Removal of fat/connective tissue and this is followed by gross cutting to approximately 12 cm×8 cm;

(iv) Followed by irrigation in physiological saline with gentle mechanical agitation;

v) Provision of a first rigid counterform (11) including holes (13)—lower counterform (FIG. 7A);

vi) fitting the first rigid counterform (11) with a suitable connecting means, e.g. screws (14) (FIG. 7B);

vii) Placement of a first permeable material layer (7b; technical fabric) centrally on the first rigid counterform (11) as a support surface without folds (FIG. 7C);

viii) Central wrinkle-free support of the pericardial tissue (8) on the first permeable material layer (7b), followed by a smoothing out of any air bubbles present in the pericardial tissue (8) (FIG. 7D);

ix) Central wrinkle-free overlay of a second permeable material layer (7a) of technical tissue on the pericardial tissue (8) (FIG. 7E);

x) central overlay of a pressure compensation layer of polyurethane foam (12) on the second permeable material layer (7a) (FIG. 7F);

xi) Precisely fitting and form-fitting support of a second rigid counterform (10) with perforations (10a) and including holes (13) (upper counterform; FIG. 7G);

xii) connecting the two counterforms (10, 11) via the screws (14) and fixing the counterforms (10, 11) by a suitable continuously adjustable retaining means, such as, for example, one or more nuts (14a) (FIG. 7H);

xiii) adjustment of a desired pressure load (application of force) between the counterforms (10, 11) via a suitable regulation of the distance between the two plates; for example, via a looser or tighter screwing (14, 14a) of both plates (10, 11). This means that the pressure load is controlled as a function of the plate spacing (10, 11), which can be implemented mechanically, hydraulically or via a suitable pneumatic system, for example;

xiv) placing the device/crosslinking unit according to FIG. 7H in a suitable receptacle/container—e.g. substantially vertically or substantially horizontally;

xv) Filling the container/receptacle with a sufficient amount of 0.5% glutaraldehyde solution such that the device/crosslinking unit is completely covered with the crosslinking solution;

xvi) Followed by chemical crosslinking for 2 days at a temperature of 37° C.;

xvii) Storage of the final processed pericardial tissue in glutaraldehyde solution or followed by any further processing.

The use of the polyurethane foam as a pressure compensation layer (12) and to transmit the force of the compressive load ensures compensation of the natural inhomogeneities of the pericardial tissue, avoiding local stress peaks. As a result, the resulting tissue has a particularly advantageous, and if required, extremely thin thickness homogeneity (see FIG. 8).

Furthermore, the foam (12) also promotes wetting of the pericardial tissue with the crosslinker solution, thus ensuring a high crosslinking quality.

By continuously reducing the plate spacing (10, 11) (e.g., by suitable screws and nuts, 14, 14a) and the associated compression of the foam (12), the final thickness of the pericardial tissue can be specifically adjusted to the requirements of a subsequent application, in particular for a medical application.

Figure 9:
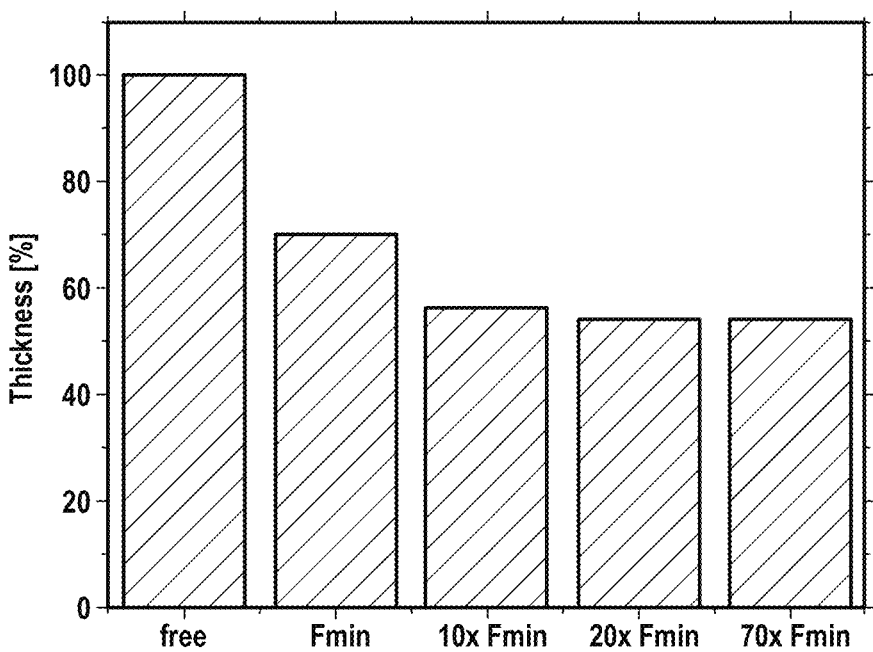
FIG. 9 shows as bar graphs the effects of a stepless increase of the pressure load (Fmin) on the tissue thickness (Thickness, top) as well as the flexibility (Deflection/Bending behavior, bottom) of the thin or ultrathin porcine pericardium produced according to the invention in direct comparison to freely and thus conventionally crosslinked porcine pericardium.
Figure 9:
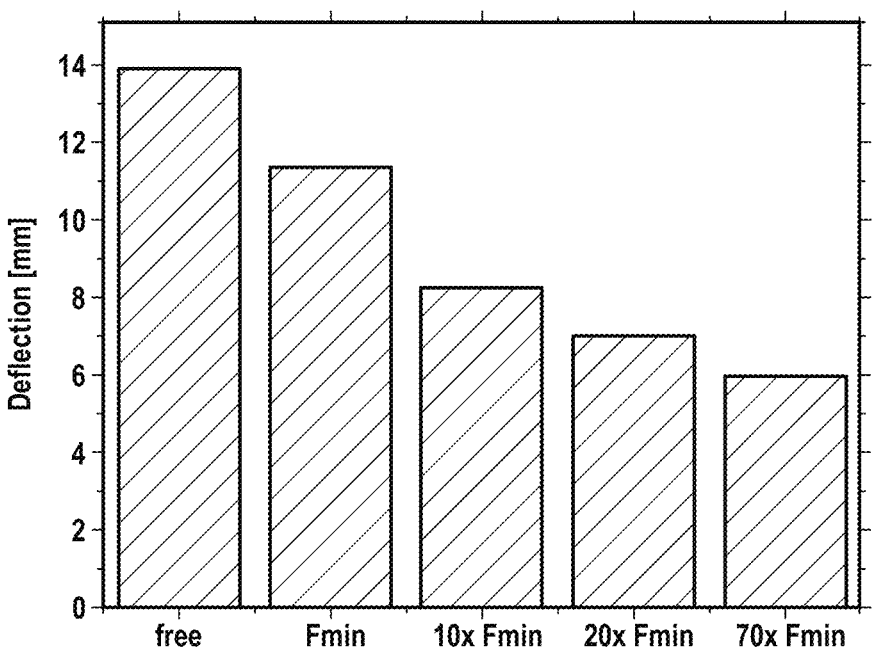
Figure 11:
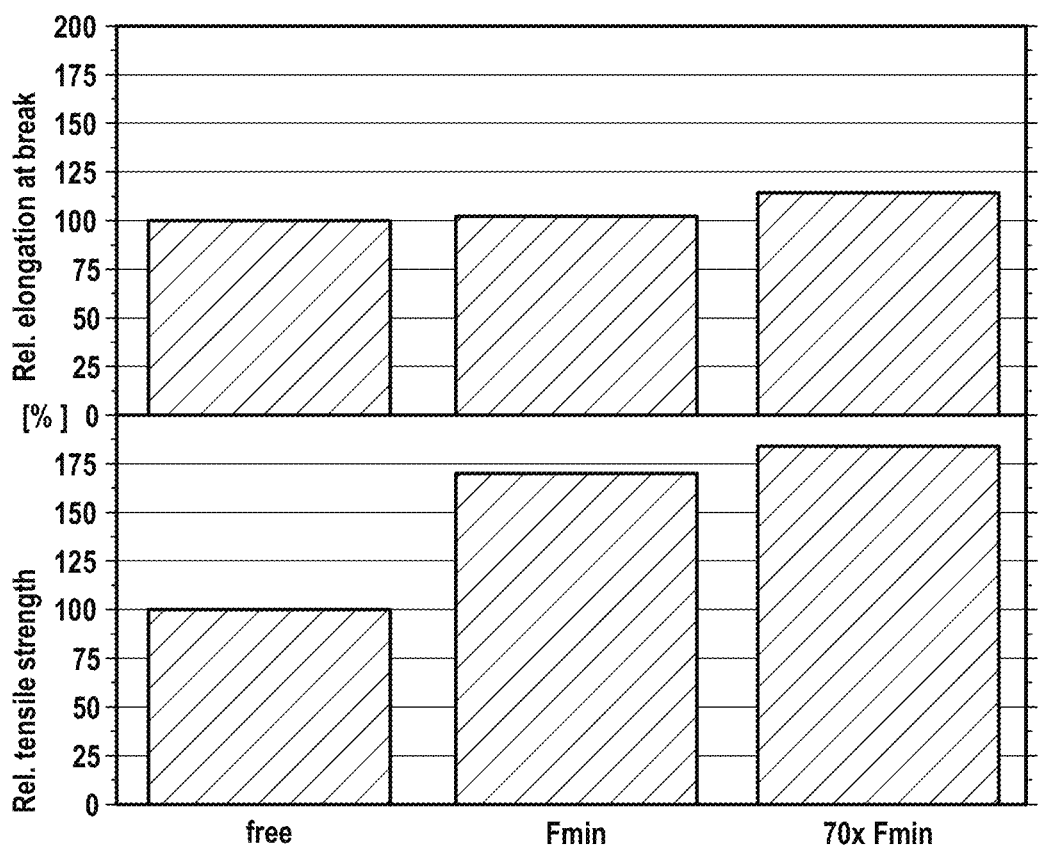
FIG. 11 shows bar graphs contrasting the elongation at break (top) and stress at break (bottom) of porcine pericardium after free crosslinking according to the prior art, porcine pericardial tissue after a process of the present invention under compressive loading as shown in FIG. 7 and the corresponding embodiment example described.

Furthermore, the flexibility of the pericardial tissue can be modified in addition to the final thickness by adjusting the plate spacing (10, 11) (see FIGS. 9 and 11).

Depending on the starting tissue used, different end thicknesses can be achieved. For example, for porcine pericardial tissue, the use of two permeable material layers (7a, 7b), e.g. of technical tissue, results in a thickness reduction of 50% already at a pressure load of about 0.1 kg/cm². Depending on the starting tissue, however, a greater thickness reduction can also be achieved by increasing the pressing force (see FIG. 9 above, FIG. 10), with complete fiber compaction representing a lower limit of the final thickness. In the case of porcine pericardium, for example, this is about 20 μm.

Since the at least one, preferably at least two permeable material layers (7a, 7b, 7c), e.g. made of technical tissue, allow large-area drainage of the stored water from the tissue even at low pressures, the load-bearing collagen fibers remain undamaged, so that the parameters of elongation at break and breaking stress are maintained (see FIG. 11) and the pericardial tissue is thus still suitable, e.g. for use in a TAVI/TAVR valve.

Variant 3—3D Crosslinking Under Pressure Load

By a suitable shaping of a rigid counterform in interaction with the pressure compensation layer (12), e.g. of a suitable foam, preferably of a polyurethane foam, it is also possible according to the invention to introduce or imprint a three-dimensional shaping into the essentially non-crosslinked starting tissue.

For example, by using the foam as a pressure compensation layer (12) in conjunction with the technical fabric of the permeable material layers (7a, 7b), a three-dimensional structure can be introduced into the tissue during the crosslinking step, while at the same time also improving the homogeneity of the tissue thickness and, if necessary, reducing the tissue thickness. The procedure is analogous to the method presented in variant 2 above, with the difference that instead of the two planar, rigid counterforms (10, 11), a rigid outer mold adapted to the desired geometry (e.g., a negative of a one-piece skirt/leaflet configuration for a TAVI/TAVR valve) and an equally adapted foam are used. Crosslinking is then also performed in a container, e.g. filled with a 0.5% glutaraldehyde solution.

In the case of large shape changes, e.g. leaflet, the technical fabric is also compression molded to achieve a better shape. Outer skirts can be made without shape embossing the mesh. Mesh made of polyester, for example, can be pre-embossed by heat in metal molds.

Figure 12A:
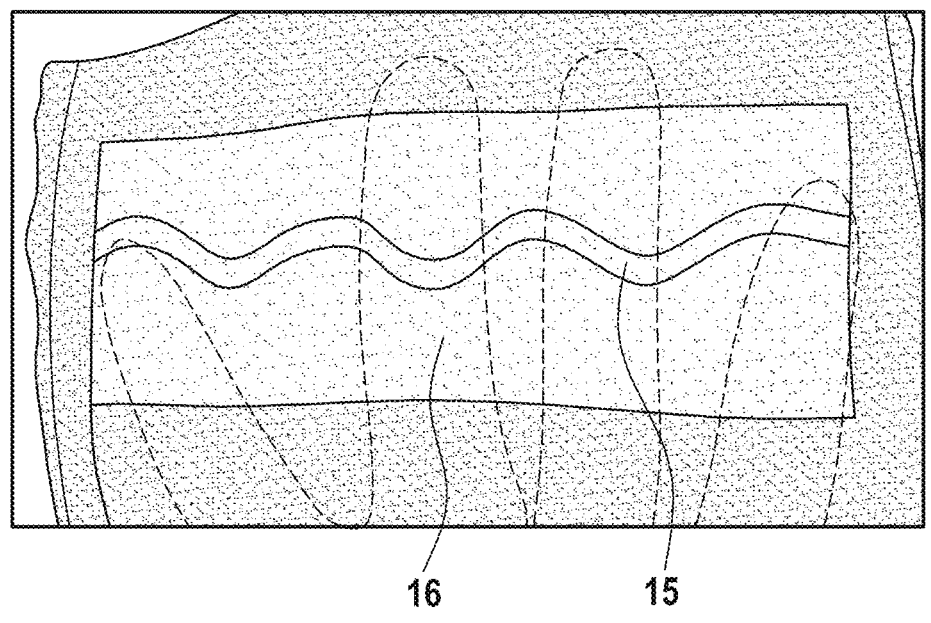
FIGS. 12A-12B show two exemplary applications for the porcine ultrathin pericardium obtained according to the present invention.
Figure 12B:
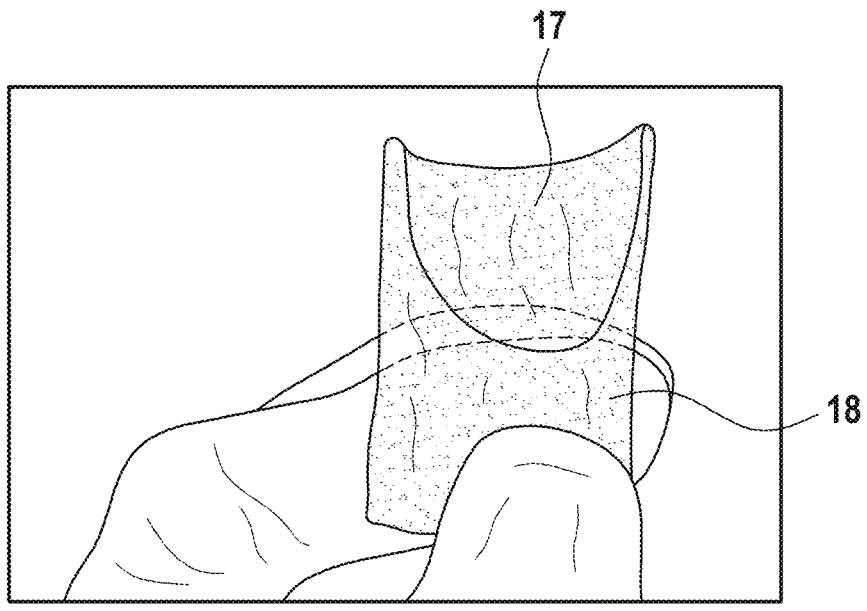

FIG. 12 shows examples of possible three-dimensional shaping. FIG. 12A shows a possible outer skirt for a TAVI/TAVR valve including an undulating protuberance with a sealing function against paravalvular leakage. FIG. 12B shows the aforementioned one-piece skirt/leaflet configuration, which, for example, eliminates the need for typically suturing individual skirt and leaflet elements.

Influence Parameters

Pressure Compensation Layer (e.g. a Foam or a Silicone)

In the context of the invention, the pressure compensation layer is characterized by the parameters: Compression hardness, density, material composition, material thickness and, if necessary, permeability. Since in some embodiments the pressure is regulated by a stepless reduction of the distance between two rigid counter-forms (10, 11), for example by suitable connecting means (14) in combination with steplessly adjustable retaining means (14a), the pressure compensation layer is of particular importance with regard to the transmission of pressure to the tissue (8) to be treated. According to the invention, compression hardness, bulk density, thickness and type of material used directly influence the maximum achievable pressure at a defined and desired distance between the counterforms (10, 11). The higher the compression hardness and bulk density are selected, and the thicker the material, the higher the pressure built up on the tissue.

Hydrophobic materials therefore appear less suitable for the pressure compensation layer with this context. Nevertheless, hydrophilic pressure compensation layers are preferred according to the invention.

A particularly preferred embodiment of the invention for the pressure compensation layer (12) includes the following set of parameters, which is very suitable for the formation of thickness-reduced tissue, in particular ultra-compact tissue:

Compression hardness: 60 kPa density: 40 kg/m$^3$

Thickness: 3 cm

Material: polyurethane foam

It is obvious to the expert that, depending on the requirements of the tissue to be treated and for the particular application, different constellations may be preferred for the pressure compensation layer.

Compression Pressure/Pressure Load

The applied compression pressure/pressure load is another important influencing parameter according to the invention. In general, at lower pressures, this results directly in higher tissue thickness. Higher pressures in turn reduce the tissue thickness; but are quasi ineffective after a certain point of thickness reduction, but still cause a stiffening of the tissue, which can be illustrated by bending behavior measurements (see FIG. 9 above compared to below). The greatest possible flexibility of the tissue obtained results from a mere chemical crosslinking in the presence of at least one, preferably at least two permeable material layers (7a, 7b, 7c), e.g. of technical fabric—without the application of a pressure (see variant 1 above).

Preferred in the context of the invention is a compression pressure/load in the range of 0.002 kg/cm$^2$ to 0.15 kg/cm$^2$.

Here, too, it is obvious to the skilled person that, depending on the requirements of the tissue to be treated and for the particular application, different compression pressures/pressure loads may be preferred.

Duration and Temperature of Pressure Crosslinking

The applied duration and temperature under pressure crosslinking is another important influencing parameter according to the invention. A suitable total duration of pressure crosslinking is in the range of 4 h to 5 days, preferably 4 h to 4 days, more preferably 3 days, even more preferably 2 days. Suitable temperatures for pressure crosslinking range from 10° C. to 50° C., preferably 25° C. to 40° C., more preferably 30° C. to 37° C., even more preferably at or around 37° C.

Thus, in some embodiments of the invention, pressure crosslinking for 2 days at 37° C. or for 4 days at room temperature as described herein is preferred.

In general, a shorter crosslinking time under pressure than, for example, under 24 h appears conceivable, but seems to lead to rather inadequate tissue properties. In particular, the compression molding then appears to be insufficient. On the other hand, a longer crosslinking time, i.e. beyond 5 days, under pressure does not seem to result in any significant advantages with regard to the tissue properties.

The duration of an optional post-crosslinking can be made more flexible in this respect, but should preferably take place over at least 3 days at 37° C. or over 5 days at room temperature.

Furthermore, in the context of the invention, an increase in temperature during chemical crosslinking (e.g., under the pressure load disclosed herein) generally leads to an acceleration of the crosslinking method. However, the denaturation temperature of the tissue to be treated should be kept well below this temperature.

Properties/Requirements for the Permeable Material Layer(s)—e.g. Made of Technical Fabric One problem of the permeable material layer(s) (7a, 7b, lac) of the technical fabric disclosed herein, for example, is to ensure a sufficient surface area for the exchange of liquids, in particular of the tissue water and the crosslinking solution, during crosslinking under pressure. This includes, on the one hand, the drainage of water from the (biological) tissue during compression/pressure loading (drainage function) and, on the other hand, the supply of the crosslinking solution to the tissue to be treated. Characteristic parameters are therefore essentially the surface properties, permeability and stiffness of the permeable material layer(s), e.g. of the technical fabric used here.

Due to the direct contact of the permeable material layer(s) (7a, 7b, 7c) with the tissue to be crosslinked, special requirements must be placed on the surface of the technical tissue, for example, such as the absence of detaching particles or also the structuring of the material layers themselves, since these may be imprinted in the (biological) tissue during crosslinking.

Preferred in the context of the invention are polyester meshes with 100-180 threads/cm. The mesh size ranges from 10 μm-60 μm, with a thickness of the technical fabric of about 40 μm-70 μm being suitable. Larger mesh sizes also lead to a sufficient exchange of fluids, but the imprinted structure on the surface of the biological tissue may then even be visible to the naked eye.

Nevertheless, in another embodiment these properties of the imprinted surfaces of the permeable material layers (7a, 7b, 7c) can also be used within the scope of the invention in a positive sense. Namely, whenever one wishes to imprint a technically functional surface on the tissue to be treated, such as, for example, a roughening of a surface or specific depressions in a surface, etc.

With respect to the foregoing entire disclosure, the present invention further includes the following embodiments, lettered in ascending order:

A. Method for the preparation of crosslinked and optionally shaped tissue, in particular crosslinked and/or shaped biological tissue, with selective adaptation of the thickness, shape and/or flexibility of the tissue, for medical applications, in particular for use as a component of a medical implant, preferably a vascular implant, more preferably an artificial heart valve or a covered stent, wherein the method includes at least the following steps:

a) providing one or more (substantially non-crosslinked) tissues including (chemically and/or biochemically) crosslinkable groups;

b) providing at least one, preferably at least two, permeable material layers configured, optionally bonded to each other, to act as at least a support surface covering the tissue and/or as at least a perfectly fitting receiving pocket for the tissue;

c) optional cutting of the tissue(s) to be crosslinked according to step a) by a suitable cutting instrument and/or a suitable cutting device;

d) placing/arranging the tissue according to step a) or c) on, in or between the permeable material layer(s) according to step b);

e) providing a container or receptacle suitable for chemical crosslinking;

f) chemically crosslinking the tissue according to step d) with the addition of a suitable crosslinking agent to the container or receptacle according to step e), preferably over a total period of at least 4 hours to a maximum of 5 days;

g) removal of the crosslinked and optionally shaped tissue according to step f);

h) optional (purely) chemical post-crosslinking by a suitable crosslinking agent.

B. Method according to embodiment A, wherein the method includes at least the following steps:

a) providing one or more (substantially non-crosslinked) tissue(s) including (chemically and/or biochemically) crosslinkable groups;

b) bonded together, to act as at least a support surface covering the tissue and/or at least a perfectly fitting receiving pocket for the tissue;

c) optionally providing a device including at least two rigid counterforms, preferably at least one of said counterforms being perforated, and configured to be connected via one or more suitable spaced apart adjustable connecting and/or retaining means, preferably one or more threaded screws with accurately fitting nuts, adjustable in distance to each other, so as to be able to exert a stepless pressure load on the tissue according to step b), and in such a way that the at least one, preferably the at least two permeable material layers provide a fluid exchange between tissue and environment;

d) optionally providing one or more pressure compensation layers, preferably one or more foam layers, which are configured to completely cover at least the tissue and at least the one or more permeable material layers as a support surface, and which are optionally placed on one or more of the permeable material layers for a snug fit, and thus come to rest between the at least two rigid counterforms;

e) optionally cutting the tissue(s) to be crosslinked according to step a) by a suitable cutting instrument and/or a suitable cutting device;

f) placing/arranging the tissue according to step a) or e) on/in the permeable material layers according to step b) and optionally thereon in the device according to step c) with an optional placing/addition of one or more of the pressure compensation layers according to step d) and wherein the rigid counterforms are gradually reduced in their distance via the adjustable connecting means/fixing means in such a way that a (continuous) pressure effect on the tissue is obtained;

g) providing a container or receptacle suitable for chemical crosslinking;

h) chemically crosslinking the arranged tissue according to step f) with the addition of a suitable crosslinking agent into the container or receptacle according to step g) over a total period of at least 4 hours up to a maximum of 5 days; or i) chemically crosslinking the arranged tissue according to step f) in said device with the optionally inserted pressure compensation layer(s) with the addition of a suitable crosslinking agent into the container or receptacle according to step g), and optionally further reducing the spacing of the rigid counterforms via the adjustable connecting means/fixing means, over a total period of at least 4 hours to a maximum of 5 days;

j) demolding/removal of the tissue crosslinked and molded according to step (h) or step (i);

k) optional (purely) chemical post-crosslinking by a suitable crosslinking agent.

C. Method according to embodiment A or B, wherein the method includes at least the following steps:

a) providing one or more (substantially non-crosslinked) tissue(s) including (chemically and/or biochemically) crosslinkable groups;

b) bonded together, to act as at least a support surface covering the tissue and/or at least a perfectly fitting receiving pocket for the tissue;

c) providing a device including at least two rigid counterforms, preferably at least one of said counterforms being perforated, and configured to be adjustable in distance to each other via one or more suitable connecting and/or retaining means adjustable in distance to each other, preferably one or more threaded screws with accurately fitting nuts, so as to be able to exert a stepless compressive load on the tissue according to step a), in such a way that the at least one, preferably the at least two permeable material layers provide a fluid exchange between tissue and environment;

d) providing one or more permeable pressure compensation layers, preferably one or more foam layers, which are configured to completely cover at least the tissue and at least the one or more permeable material layers as a support surface, and which are optionally placed on one or more of the permeable material layers for a snug fit, and thus come to rest between the at least two rigid counterforms;

e) optionally cutting the tissue(s) to be crosslinked according to step a) by a suitable cutting instrument and/or a suitable cutting device;

f) placing/arranging the tissue according to step a) or e) on/in the permeable material layers according to step b), which have previously been placed in the device according to step c), followed by placing/adding one or more of the permeable pressure compensation layers according to step d) in the device according to step c), and whereupon the rigid counterforms are gradually reduced in their distance via the adjustable connecting means/restraining means in such a way that a (continuous) pressure effect on the tissue is created;

g) optionally providing a container or receptacle suitable for chemical cross-linking;

h) chemically crosslinking the arranged tissue according to step f) in said device with the addition of a suitable crosslinking agent into the container or receptacle according to step g), and wherein optionally the rigid counter-forms are further reduced in their distance stepwise via the adjustable connecting means/fixing means, over a total period of at least 4 hours up to a maximum of 5 days;

i) demolding/removal of the crosslinked and molded tissue after step (h);

j) Optional (purely) chemical post-crosslinking using a suitable crosslinking agent.

D. The method according to any of the preceding embodiments, wherein the crosslinking agent is an aldehyde-containing solution or is selected from the group consisting of glutaraldehyde, carbodiimide, formaldehyde, glutaraldehyde acetals, acyl azides, cyanimide, genipin, tannin, pentagalloyl glucose, phytate, proanthocyanidin, reuterin, and/or epoxy compounds.

E. The method according to any of the preceding embodiments, wherein the crosslinking agent is glutaraldehyde or a glutaraldehyde solution, preferably a glutaraldehyde solution having a concentration of between 0 vol % and 2 vol % glutaraldehyde, more preferably between 0.01 vol % and 1 vol % glutaraldehyde, most preferably 0.5 vol % glutaraldehyde.

F. The method according to any one of the preceding embodiments, wherein the tissue has been subjected to a pretreatment including an optional decellularization, preferably with a solution containing surfactin and deoxycholic acid, and optionally a pre-crosslinking, preferably with a solution containing glutaraldehyde.

G. The method according to any of the preceding embodiments, wherein the tissue is rinsed at least once with a suitable solution, in particular a salt solution and/or an alcohol solution, before and/or after the crosslinking, the optional pre-crosslinking and/or the optional post-crosslinking H. The method according to any of the preceding embodiments, wherein the method further includes performing a structural stabilization step on the, optionally decellularized, tissue before or after the crosslinking, the optional pre-crosslinking and/or the optional post-crosslinking I. The method according to embodiment H, wherein the structural stabilization step is performed on the, optionally decellularized, tissue after the crosslinking, after the optional pre-crosslinking, or after the optional post-crosslinking J. The method according to any of the preceding embodiments H or I, wherein the structure stabilization step includes exposing the, optionally decellularized, tissue to at least one solution, but preferably at least two different solutions, wherein one solution includes glycerol and another solution includes polyethylene glycol.

K. The method according to embodiment J, wherein exposure to one or more of the solutions lasts from 5 minutes to 2 hours.

L. The method according to any of the preceding embodiments, further including drying the tissue in a suitable environment of constant low relative humidity or in a climate chamber by reducing the relative humidity, optionally from 95% to 10% over 10 to 14 hours at 30° C. to 39° C., preferably over 12 hours at 37° C.

M. The method according to any one of embodiments J to L, wherein of the at least two different solutions, a first solution includes polyethylene glycol having an average molecular weight between 150 g/mol and 600 g/mol; and a second solution is an aqueous solution of polyethylene glycol having an average molecular weight between 200 g/mol and 6000 g/mol.

N. The method according to any one of embodiments J to M, wherein of the at least two different solutions, a first solution includes polyethylene glycol having an average molecular weight between 200 g/mol and 300 g/mol, preferably 200 d/mol; and a second solution is an aqueous solution of polyethylene glycol having an average molecular weight between 200 g/mol and 1000 g/mol, preferably 400 g/mol.

O. The method according to any of the preceding embodiments, wherein the method additionally includes removal of alpha-gal epitopes by use of a suitable alpha-galactosidase.

P. The method according to embodiment 0, wherein the alpha-galactosidase is obtained from green coffee bean (GCB).

Q. The method according to embodiment 0, wherein the alpha-galactosidase is derived from *Cucumis melo*.

R. The method according to any of the preceding embodiments, wherein the chemical crosslinking takes place over a period of time in the range of 4 h to 5 days, preferably 4 h to 4 days, more preferably 3 days, even more preferably over 2 days.

S. The method according to any of the preceding embodiments, wherein the chemical crosslinking takes place at a temperature in the range of 10° C. to 50° C., preferably 25° C. to 40° C., more preferably 30° C. to 37° C., even more preferably at or around 37° C.

T. The method according to any one of the preceding embodiments, wherein the optional post-crosslinking is carried out for at least 3 days at 37° C. or for 5 days at room temperature.

U. The method according to any one of the preceding embodiments, wherein the permeable material layers include a technical fabric.

V. The method according to any one of the preceding embodiments, wherein the permeable material layers have a mesh size in the range of 10 μm to 60 μm.

W. The method according to any one of the preceding embodiments, wherein the permeable material layers have a thickness/height in the range of 40 μm to 70 μm.

X. The method according to any one of the preceding embodiments, wherein the permeable material layers include a polyester mesh having 100 threads/cm to 180 threads/cm and a mesh size in the range of 10 μm to 60 μm and a thickness/height in the range of 40 μm to 70 μm.

Y. The method according to any of embodiments B to X, wherein the pressure compensation layer has a compression hardness in the range of 20 kPa to 80 kPa, preferably 30 kPa to 70 kPa, more preferably kPa to 60 kPa, even more preferably 60 kPa.

Z. The method according to any one of embodiments B to X, wherein the pressure compensation layer has a Shore hardness A in the range of 5 to 70, preferably 10 to 50, more preferably 15 to 30, still more preferably 20.

AA. The method according to any one of embodiments B to Z, wherein the pressure compensation layer has a bulk density in the range of 10 kg/m$^3$ to 60 kg/m$^3$, preferably 20 kg/m$^3$ to 50 kg/m$^3$, more preferably kg/m$^3$ to 40 kg/m$^3$, even more preferably 40 kg/m$^3$.

BB. The method according to any of embodiments B to Z, wherein the pressure compensation layer has a thickness/height in the range of 1 cm to 5 cm, preferably 2 cm to 4 cm, more preferably 3 cm to 4 cm, even more preferably 3 cm.

CC. The method obtained according to any one of embodiments B to BB, wherein the pressure compensation layer is a polyurethane foam, having a compression hardness of 60 kPa, a density of 40 kg/m$^3$, and a thickness of 3 cm.

DD Tissue obtained according to one of the preceding embodiments.

EE. Tissue obtained according to embodiments DD or obtained by a method according to any one of the embodiments A to CC having a thickness of less than 80 μm, preferably between 80 and 20 μm or between 25 μm and 20 μm.

FF. Tissue according to embodiments DD or EE or obtained by a method according to any one of the embodiments 1 to 29, which has a thickness homogeneity with a variation of the order of 40 μm with a measurement tolerance in thickness per measurement of ±5 μm.

GG. Tissue according to embodiments DD to FF or obtained by a method according to any one of the embodiments A to CC wherein the (ultra-compact) thickness homogeneity is characterized by a (substantially constant) thickness of the tissue of below 40% of the initial thickness of the tissue.

HH. Medical implant, preferably having a hollow cylindrical base structure, wherein in and/or on a surface of the base structure the tissue according to embodiments DD to GG is arranged, which in the implanted state of the medical implant is intended and arranged to contact an anatomical structure of a patient, in particular a vessel wall, in particular a vessel, to which the medical implant has been implanted.

II. The medical implant according to embodiment HH, wherein the implant is a prosthetic heart valve including an artificial heart valve made of said tissue and/or a seal made of said tissue, which is attached, preferably sutured, to an expandable or self-expanding base body implantable by catheter.

JJ. The medical implant according to one of embodiments HH or II, wherein the medical implant is selected from the group consisting of an artificial heart valve, in particular an artificial aortic valve, a coronary or peripheral vascular stent, in particular a covered stent and/or a stent graft.

KK. The medical implant according to embodiment JJ, wherein the tissue is selected from the group consisting of pericardium, ligaments, tendon, cartilage, bone, skin.

LL. Medical implant including the tissue according to any one of embodiments DD to HH or obtained by the method according to any one of the embodiments A to CC.

MM. The medical implant according to embodiment LL, wherein the medical implant is a cardiovascular implant, a endovascular prostheses, an endoprostheses, an esophageal implant, a bile duct implant, a dental implant, an orthopedic implant, a sensory implant, a neurological implant a microchip containing implant.

NN. The medical implant according to embodiment MM, wherein the medical implant is a stent, a vascular stent, a drug eluting stent, a pulmonary valve stent, a bile duct stent, a peripheral stent, a mitral stent, a stent graft, a venous valve, a tooth implant, a bone implant, a glucose sensor implant, a neurostimulator, a cochlear implant, an endoprostheses for closing persistent foramen ovale, an endoprostheses for closing an atrial septal defect, a left atrial appendage closure device, a pacemaker, a leadless pacemaker, a defibrillator, a prosthetic heart valve, preferably a TAVI/TAVR valve.

OO. Tissue according to embodiments DD to HH or obtained by the method according to any one of the embodiments A to CC for medical use, in particular for use in a cardiovascular implant, a endovascular prostheses, an endoprostheses, an esophageal implant, a bile duct implant, a dental implant, an orthopedic implant, a sensory implant, a neurological implant a microchip containing implant.

PP. Tissue according to embodiments DD to HH or obtained by the method according to any one of the embodiments A to CC for medical use, in particular for use in a stent, a vascular stent, a drug eluting stent, a pulmonary valve stent, a bile duct stent, a peripheral stent, a mitral stent, a stent graft, a venous valve, a tooth implant, a bone implant, a glucose sensor implant, a neurostimulator, a cochlear implant, an endoprostheses for closing persistent foramen ovale, an endoprostheses for closing an atrial septal defect, a left atrial appendage closure device, a pacemaker, a leadless pacemaker, a defibrillator, a prosthetic heart valve, preferably a TAVI/TAVR valve.

QQ. Device for the preparation of crosslinked and optionally (three dimensionally) shaped tissue including
    at least two (rigid) counterforms, preferably at least one of said counterforms being perforated,
    connection means for connecting the counterforms with each other, preferably in a form fit and force fit manner,
    adjustment means for adjusting the distance of the counterforms to each other,
    one or more (permeable) pressure compensation layer(s) being arranged between the at least two counterforms
    one or more permeable material layer(s) being arranged between the at least two counterforms and preferably between two permeable pressure compensation layers.

RR. The device according to embodiment QQ, wherein one or more permeable pressure compensation layer is a solid foam layer, preferably a polymeric foam layer, preferably a polyurethane foam.

SS. The device according to embodiment QQ or RR, wherein one or more permeable material layer is an organic polymeric layer, preferably a polyester layer.

TT. The device according to any one of the embodiments QQ to SS, wherein one or more permeable material layer has a thickness of 40 μm to 70 μm.

UU. The device according to any one of the embodiments QQ to TT, wherein the adjustment means are able to apply a compressive load on at least one of the counterforms, preferably to all counterforms.

VV. The device according to any one of the embodiments QQ to UU, wherein adjustment means are one or more threaded screws with (accurately) fitting nuts.

WW. The device according to embodiment UU, wherein adjustment means are able to apply a stepless compressive load on the tissue counterforms, preferably by a motor being connected to the adjustment means.

FIG. 1 shows an example of a typical tissue surface of pericardium (2) on a substrate (1) after chemical crosslinking with glutaraldehyde solution according to the state of the art using rigid moldings on both sides. The double-sided rigid molded bodies are not capable of compensating for the inhomogeneity in tissue thickness that is naturally always present. In areas of the tissue with a higher thickness (3), this results in pressure peaks which cause partial fiber compaction and the associated stiffening of the tissue. Visually, these pressure points can be identified as transparent areas on the tissue surface (4, 5). Air bubbles trapped between the two moldings also have this effect (5). In addition, the rigid molded bodies hinder the access of the crosslinking solution to the tissue, resulting in poorer crosslinking quality of the tissue.

FIG. 2 shows a first exemplary embodiment of the method according to the invention with (purely) planar chemical crosslinking of pericardial tissue—without pressure load—between two interconnected (6) permeable material layers (7a, 7b), presently connected via seams in area 6, which are set at the left and rear edges in such a way as to form a kind of receiving pocket to receive and completely cover the pericardial tissue (8) over the entire area. The use of the two permeable material layers (7a, 7b), e.g. made of technical fabric, allows the pericardium (8) to be crosslinked without folds and without pretensioning the collagen fibers, resulting in a significantly more flexible but chemically crosslinked pericardial tissue. For this purpose, the pericardial tissue (8) is placed and arranged between the permeable material layers (7*a*) and (7*b*) after mechanical preparation, and in this state it is placed/positioned vertically in a suitable container, e.g. in a 0.5% glutaraldehyde solution, and crosslinked, or alternatively laid out flat in a container and covered with the glutaraldehyde solution. This method thus provides a flexible and wrinkle-free cross-linked pericardium, which still exhibits the original thickness distribution inherent to the biological starting material. In this variant, the technical fabric of the two permeable material layers (7*a*) and (7*b*) does not primarily serve to provide a flat water drainage option in the sense of drainage, but rather to stabilize the shape for wrinkle-free crosslinking with simultaneous optimized accessibility of the fixation solution via the permeable material layers (7*a*) and (7*b*).

Various implementations of the crosslinking methods according to the invention without pressure can be seen in the following figures, and are explained in a similar manner as above.

Figure 3:
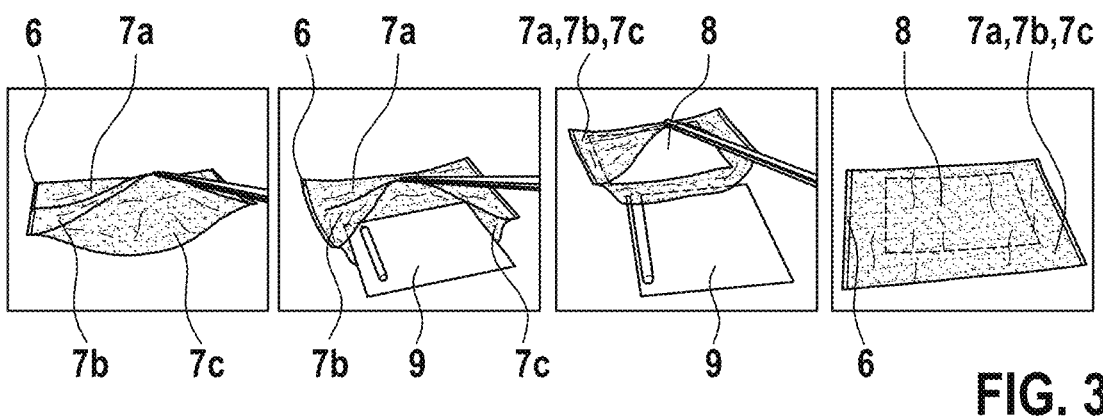
FIG. 3 shows a second exemplary embodiment of the method according to the invention with purely planar chemical crosslinking of pericardial tissue—without pressure load.

FIG. 3 shows a second exemplary embodiment of the method according to the invention with purely planar chemical crosslinking of pericardial tissue—without pressure load—but with three interconnected (6) permeable material layers (7*a*, 7*b*, 7*c*), presently connected by seams in area 6, which are set at the left, rear and right edges in such a way as to form two receiving pockets for the pericardial tissue (8), so as to receive and completely cover it over the entire surface. Furthermore, FIG. 3 shows an auxiliary device (9), which is shaped like a transparent card made of a plastic material with a left-hand grip, and by whose surface a piece of tissue can be transported in a planar and wrinkle-free manner and placed in the receiving pocket—preferably without touching the tissue itself. The use of the three permeable material layers (7*a*, 7*b*, 7*c*), e.g. made of technical tissue, allows two pericardial tissues (8) to be crosslinked simultaneously without pretensioning the collagen fibers, resulting in a significantly more flexible but chemically crosslinked pericardial tissue. It is obvious to the skilled person that four, five, six or more receiving pockets can also be provided in a suitable manner in order to crosslink more tissue samples simultaneously without pressure according to the invention.

For this purpose, the pericardial tissue (8) is placed and arranged between the permeable material layers (7*a*) and (7*b*) as well as (7*b*) and (7*c*) after mechanical preparation, and in this state, for example in a glutaraldehyde solution, is placed vertically in a suitable container and crosslinked, or alternatively laid out flat in a container and covered with the glutaraldehyde solution. This method thus provides a flexible and wrinkle-free cross-linked pericardium, which still exhibits the original thickness distribution inherent in the biological starting material. In this variant, too, the technical fabric of the three permeable material layers (7*a*), (7*b*) and (7*c*) does not primarily serve to provide a surface water drainage option in the sense of drainage, but rather to stabilize the shape for wrinkle-free crosslinking with simultaneous optimized accessibility of the fixation solution via the permeable material layers (7*a*), (7*b*) and (7*c*).

Figure 4:
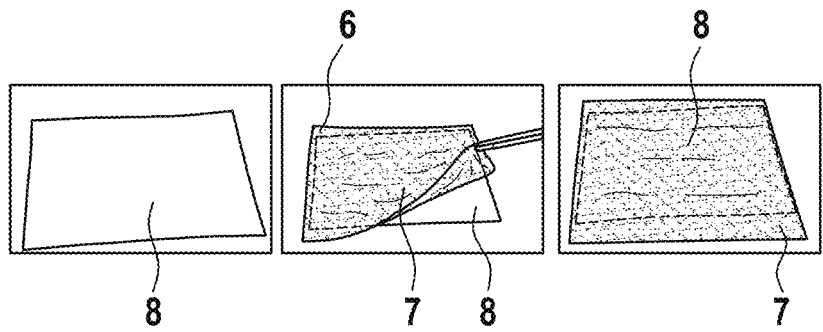
FIG. 4 shows a third exemplary embodiment of the method according to the invention with purely planar chemical crosslinking of pericardial tissue—without pressure load.

FIG. 4 shows a third exemplary embodiment of the method according to the invention with purely planar chemical crosslinking of pericardial tissue—without pressure load—but using only one permeable material layer (7). The permeable material layer (7) must be designed in such a way that it can completely cover the entire surface of the pericardial tissue (8). The use of a permeable material layer (7), e.g. made of technical fabric, already enables fold-free crosslinking of the pericardium (8) without pretensioning of the collagen fibers, resulting in a significantly more flexible but chemically crosslinked pericardial tissue (8). For this purpose, after mechanical preparation, the pericardial tissue (8) is laid flat on a suitable base, e.g. in a container, and the permeable material layer (7) is placed on the tissue in a form-fitting manner, or vice versa, in which case the pericardium is placed on a mesh as a technical fabric, and in this state covered with this crosslinking agent with the addition of, for example, a 0.5% glutaraldehyde solution. This method also provides a flexible and wrinkle-free crosslinked pericardium, which still has the original thickness distribution inherent to the biological starting material. In this variant, too, the technical fabric of the permeable material layer (7) does not primarily serve to provide a flat water drainage option in the sense of drainage, but rather to stabilize the shape for wrinkle-free crosslinking with simultaneous optimized accessibility of the fixation solution via the permeable material layer (7).

Figure 5:
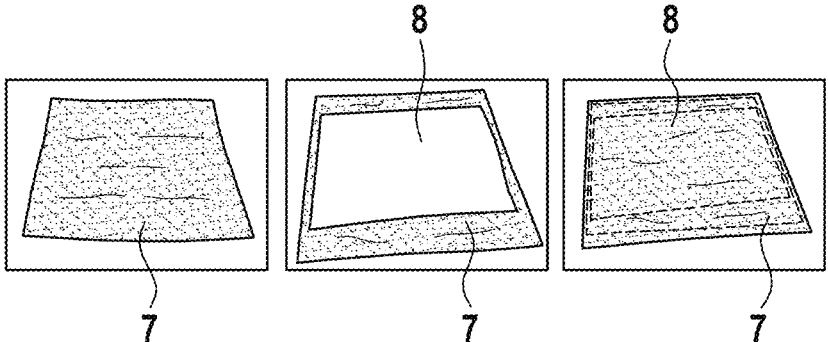
FIG. 5 shows a fourth exemplary embodiment of the method according to the invention with purely planar chemical crosslinking of pericardial tissue—without pressure load.

FIG. 5 shows a fourth exemplary embodiment of the method according to the invention with purely planar chemical crosslinking of pericardial tissue—without pressure load—between two loose permeable material layers (first layer (7) on the left, second layer (7) on the right), which are placed loosely one above the other in such a way that the pericardial tissue (8) lying quasi in a "sandwich" between them is completely covered over the entire surface. The use of the two permeable material layers (first layer (7) on the left, second layer (7) on the right), e.g. made of technical fabric, makes it possible to crosslink the pericardium (8) without folds and without pretensioning the collagen fibers, resulting in a significantly more flexible but chemically crosslinked pericardial tissue. For this purpose, after mechanical preparation, the pericardial tissue (8) is placed and arranged between the loose permeable material layers (7 left figure) and (7 right figure), and in this state it is laid out flat in a 0.5% glutaraldehyde solution in a suitable container, for example, and covered with the glutaraldehyde solution. This method also provides a flexible and wrinkle-free crosslinked pericardium, which still exhibits the original thickness distribution inherent to the biological starting material. The technical fabric of the two loose permeable material layers (first layer (7) left figure, second layer (7) right figure) also serve in this variant ostensibly not a two-dimensional water drainage possibility in the sense of a drainage, but rather the form stabilization for a wrinkle-free crosslinking with simultaneous optimized accessibility of the fixation solution via the two loose permeable material layers (7).

Another variant would be to subsequently weld the screens as the final step. That is, 1st layer of mesh, lay on pericardium, 2nd layer of mesh, then weld the mesh all around instead of suturing. Advantage: easier application and safe handling during crosslinking.

FIG. 6 shows in schematic cross-section the structure/arrangement of various material layers in a device/crosslinking unit suitable for a basic embodiment of the methods of the invention with pressure loading (the arrows represent the pressure loading schematically). Essential to these methods is a further modification of the crosslinking step. As can be seen in FIG. 6, the crosslinking of the exemplary pericardial tissue (8) takes place while it is arranged/placed in a device/crosslinking unit consisting of two rigid but optionally perforated counterforms (10, 11), a polyurethane foam (e.g. 10-30 mm in height) as an additional pressure compensation layer (12), and two permeable material layers of e.g. technical fabric (7*a*, 7*b* with drainage function; e.g. 50 μm polyester with 40 μm meshes). The device/crosslinking unit assembled in this way is placed in a suitable container with, for example, 0.5% glutaraldehyde solution for chemical crosslinking so that the mold is completely covered by the crosslinking solution.

According to the invention, the technical fabric as a permeable material layer has essentially two functions: (i) Draining the water from the tissue when the external pressure is applied; (ii) Improving the accessibility of a crosslinking solution to the tissue during the pressed crosslinking. So not only a drainage function, because of the fiber structure, the technical fabric, such as mesh, additionally "conducts" liquid from one position to another.

The use of the permeable material layers (7a, 7b), e.g. made of technical fabric, enables through its permeable properties on the one hand that water present in the pericardial tissue can be removed with comparatively low pressure (in the sense of drainage), and on the other hand ensures sufficient accessibility of the crosslinking solution to the pericardial tissue (8). This can optionally be promoted by the fact that the rigid counterforms (10, 11) are either both or only one of them, preferably the upper one (1), additionally perforated and also facilitate access to the pericardial tissue (8).

By compressing the e.g. polyurethane foam as a pressure compensation layer (12) under an applied pressure load between the rigid counterforms (10, 11), a desired and continuously adjustable pressure is exerted on the pericardial tissue (8). The water present in the pericardial tissue escapes via the layers of the technical fabric as permeable material layers (7a, 7b) already during the assembly of the previously described device/crosslinking unit. Since the entire device/crosslinking unit is placed in a container with, for example, 0.5% glutaraldehyde solution directly after assembly, by which, among other things, interfibrillar crosslinks are formed, the compacted state of the pericardial tissue (8) is permanently maintained. For example, according to the invention, ultra-compact and thus very thin tissue can be provided by applying an appropriately high pressure to the tissue to be treated via the aforementioned device/crosslinking unit; for example, pericardium with an initial thickness of 200 μm, which can be compacted to a final thickness of up to 20 μm.

The use of the pressure compensation layer (12), e.g. polyurethane foam or a silicone mat, serves to transfer the force of the applied pressure of the rigid counterforms (10, 11) and ensures compensation of the natural inhomogeneity of the tissue (8), thus avoiding local stress peaks. The resulting tissue thus exhibits improved thickness homogeneity (see FIG. 8). Furthermore, in addition, such a pressure compensation layer promotes the wetting of the pericardial tissue (8) with the crosslinker solution, thus ensuring a high crosslinking quality. By continuously reducing the plate spacing of the counterforms (10, 11) and the associated compression of the foam (12), the final thickness of the pericardial tissue (8) can be specifically adjusted to the requirements of a subsequent application, in particular for a medical application as an implant FIG. 7A-H schematically show the individual method steps for setting up the device/crosslinking unit described in FIG. 6 for producing a planar, e.g. ultra-compact pericardial tissue. FIG. 7A shows a lower rigid counterform (11) with several holes (13) as an initial stage. FIG. 7B shows the lower counterform (11), whereby all holes (13) are equipped with a continuously adjustable connecting means, e.g. a screw (14), in such a way that the screws themselves embody quasi joining rails, by which the above counterform (10) can be connected to the lower counterform (10), e.g.

with an accurate fit and a positive fit. In FIG. 7C, a first layer of permeable material (7b), e.g. of technical fabric, is placed in the center of the device without folds. In FIG. 7D, the pericardial tissue (8) is placed on top of the first layer of permeable material (7b), e.g. of technical tissue, without folds in the center. In FIG. 7E, a second layer of permeable material (7a), e.g. of technical fabric, is placed without folds centrally in the device over the pericardial tissue (8) and thus also over the first permeable material layer (7b). In FIG. 7F, a pressure compensation layer of polyurethane foam (12) is placed centrally in the device, and thus comes to rest above the second permeable material layer (7a), above the pericardial tissue (8), and above the first permeable material layer (7b). In FIG. 7G, the upper rigid counterform (10) with perforations (10a) is precisely and positively joined over the holes also present in (10) and the screws (14). In FIG. 7H, the screws (14) are each connected with a nut (14a) as a connecting means in such a way that the screw connection via the nuts (14a) allows a pressure load to be set on all material layers and the tissue in the device and also to be released again. In other words, the distance between the rigid counterforms (10, 11) can be selectively and continuously adjusted via the connecting means (14, 14a) to suit the situation, depending on the tissue to be treated and the crosslinking solution. With the structure of FIG. 7H, an exemplary device is completed in such a way that it can be positioned either substantially vertically or alternatively substantially horizontally in a container with suitable crosslinking agent, and can be completely covered by crosslinking agent.

Figure 8:
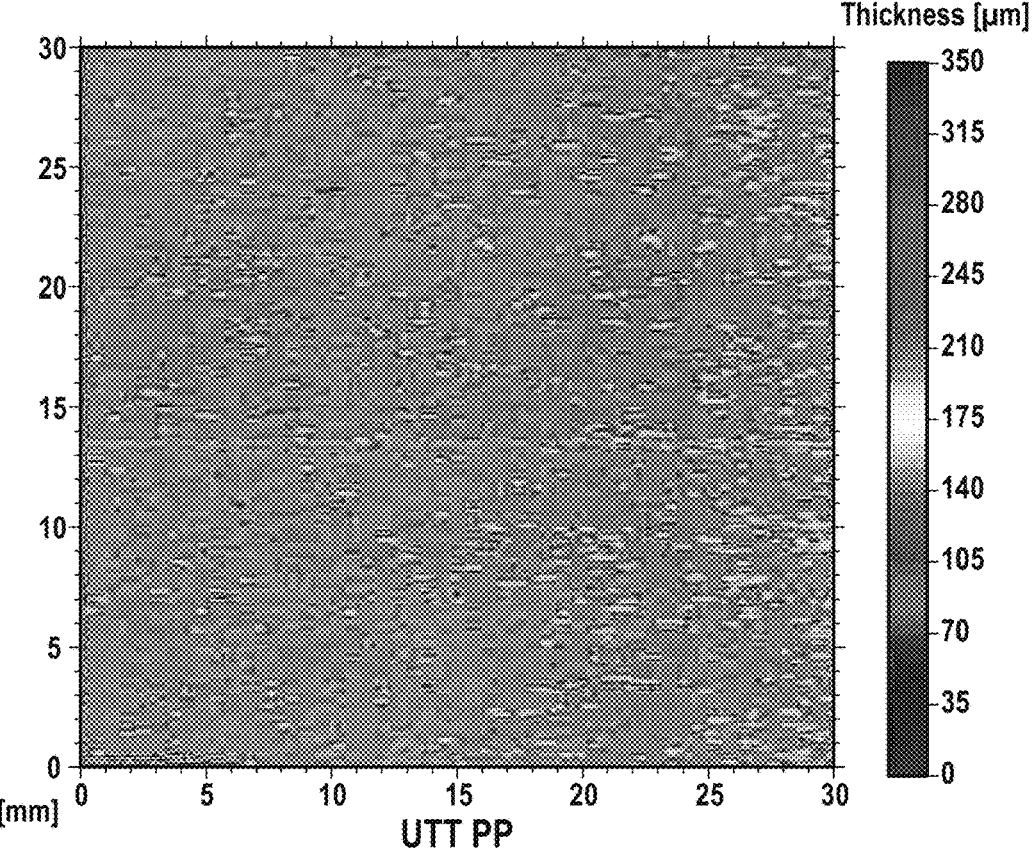
FIG. 8 shows the results of an analysis of the thickness differences of an ultrathin porcine pericardium (UTT PP; top) obtained after a process according to the invention under pressure load.
Figure 8:
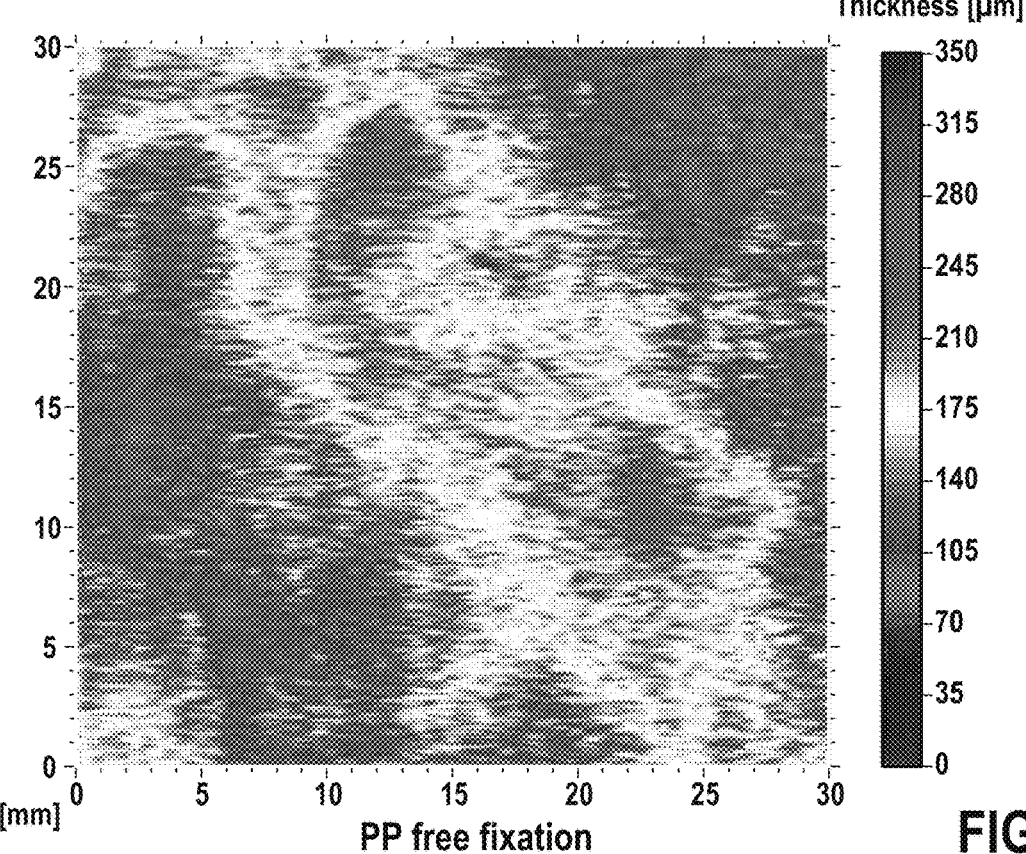

FIG. 8 shows the results of an analysis of the thickness differences of an ultrathin porcine pericardium (UTT PP; top) obtained after a process according to the invention under pressure load, as explained for example in FIG. 7 and the corresponding embodiment examples, in direct comparison with conventional porcine pericardium tissue after free chemical crosslinking (PP free fixation; bottom).

FIG. 9 shows as bar graphs the effects of a stepless increase of the pressure load (Fmin) on the tissue thickness (Thickness, top) as well as the flexibility (Deflection/Bending behavior, bottom) of the thin or ultrathin porcine pericardium produced according to the invention in direct comparison to freely and thus conventionally crosslinked porcine pericardium.

Figure 10:
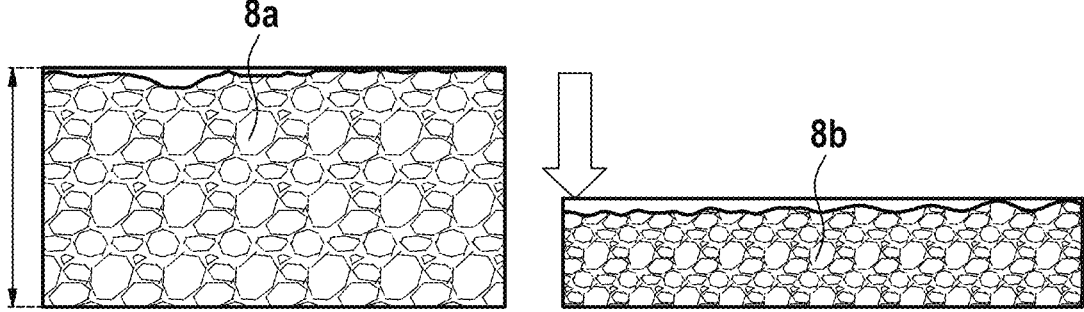
FIG. 10 schematically shows the results of a scanning electron micrograph (SEM) in terms of thickness comparison of a native porcine pericardium as initial tissue.

FIG. 10 schematically shows the results of a scanning electron micrograph (SEM) in terms of thickness comparison of a native porcine pericardium as initial tissue (8a, left, approx. 250 μm thickness), and the same porcine pericardium ultra-thinly compacted and crosslinked under pressure load (8b, right, arrow symbolizes the effect of the pressure, approx. 80 μm thickness corresponds to a. 70% thickness reduction) after a process according to the invention from FIG. 7 in connection with the corresponding embodiment example.

FIG. 11 shows bar graphs contrasting the elongation at break (top) and stress at break (bottom) of porcine pericardium after free crosslinking according to the prior art, porcine pericardial tissue after a process of the present invention under compressive loading as shown in FIG. 7 and the corresponding embodiment example described.

FIG. 12 shows two exemplary applications for the porcine ultrathin pericardium obtained according to the present invention. FIG. 12A shows a waveform (15) embossed into the ultrathin pericardium of a TAVI/TAVR valve outer skirt (16) with a three-dimensional protrusion, which can seal against paravalvular leakage in the sense of a sealing line on the outer skirt. FIG. 12B shows a skirt (18)-leaflet (17)

combination 3D-formed from ultrathin pericardium with imprinting of a 3D shape (valve fold (17) and skirt rounding (18)) during chemical crosslinking. This opens up the possibility, for example, of providing a TAVI/TAVR valve with three 3D-preformed skirt/leaflet combinations made of ultrathin pericardium instead of the six conventional pericardial components used to date, whereby one skirt element is always sutured to a leaflet and only then in turn is sutured to form the complete valve unit.

The invention claimed is:

1. A method for the preparation of crosslinked tissue, comprising:

providing tissue comprising chemically and/or biochemically crosslinkable groups;

providing at least one permeable material layer configured to act as a support surface covering the tissue and/or a receiving pocket for the tissue;

placing the tissue on the support surface or in the receiving pocket;

providing one or more pressure compensation layers, which are configured to partially or completely cover at least the tissue and the at least one permeable material layer;

chemically crosslinking the tissue with a suitable crosslinking agent;

removing of the crosslinked tissue from the support surface or the receiving pocket;

providing a device comprising at least two rigid counterforms, at least one of said counterforms being perforated, the device being configured to exert a stepless pressure load on the tissue in such a way that the at least one permeable material layer provides a fluid exchange between tissue and environment, wherein the one or more pressure compensation layers comprise one or more foam layers provided to rest between the at least two rigid counterforms; and gradually adjusting the rigid counterforms in such a way that a continuous pressure effect on the tissue is obtained.

2. The method according to claim 1, wherein:

the at least one or more foam layers comprise two form layers and the method comprises cutting the tissue prior to placing the tissue, and wherein the at least two counterforms are adjustable in relative distance to each other via threaded screws with accurately fitting nuts, so as to be able to exert a stepless compressive load on the tissue.

3. The method according to claim 1, wherein the crosslinking agent is an aldehyde-containing solution or is selected from the group consisting of glutaraldehyde, carbodiimide, formaldehyde, glutaraldehyde acetals, acyl azides, cyanimide, genipin, tannin, pentagalloyl glucose, phytate, proanthocyanidin, reuterin, and/or epoxy compounds.

4. The method according to claim 1, wherein the crosslinking agent is glutaraldehyde.

5. The method according to claim 1, comprising preliminary decellularization of the tissue before the placing.

6. The method according to claim 1, comprising structurally stabilizing the tissue before or after the crosslinking.

7. The method of claim 6, wherein the structurally stabilizing is performed after the crosslinking.

8. The method according to claim 1, wherein the structurally stabilizing comprises exposing the tissue to glycerol and/or polyethylene glycol.

9. A method for the preparation of crosslinked tissue, comprising:

providing tissue comprising chemically and/or biochemically crosslinkable groups;

providing at least one permeable material layer configured to act as a support surface covering the tissue and/or a receiving pocket for the tissue;

placing the tissue on the support surface or in the receiving pocket;

providing one or more pressure compensation layers, which are configured to partially or completely cover at least the tissue and the at least one permeable material layer;

chemically crosslinking the tissue with a suitable crosslinking agent; and removing of the crosslinked tissue from the support surface or the receiving pocket, wherein the at least one permeable material layer comprises a technical fabric.

10. A method for the preparation of crosslinked tissue, comprising:

providing tissue comprising chemically and/or biochemically crosslinkable groups;

providing at least one permeable material layer configured to act as a support surface covering the tissue and/or a receiving pocket for the tissue;

placing the tissue on the support surface or in the receiving pocket;

providing one or more pressure compensation layers, which are configured to partially or completely cover at least the tissue and the at least one permeable material layer;

chemically crosslinking the tissue with a suitable crosslinking agent; and removing of the crosslinked tissue from the support surface or the receiving pocket, wherein the at least one permeable material layer comprises a mesh size in the range of 10 to 60 µm.

11. Collagen containing biological tissue having a thickness homogeneity with a variation of 40 µm or less, with a measurement tolerance in thickness per measurement of ±5 µm, wherein the collagen containing biological tissue is obtained by a method comprising steps of:

providing collagen containing biological tissue comprising chemically and/or biochemically crosslinkable groups;

providing at least one permeable material layer configured to act as a support surface covering the tissue and/or a receiving pocket for the tissue;

placing the tissue on the support surface or in the receiving pocket;

providing one or more pressure compensation layers, which are configured to partially or completely cover at least the tissue and the at least one permeable material layer;

chemically crosslinking the tissue with a suitable crosslinking agent; and removing of the crosslinked tissue from the support surface or the receiving pocket.

12. The collagen containing biological tissue according to claim 11 having a thickness between 80 and 20 µm.

13. The collagen containing biological tissue according to claim 12, having a thickness between 25 and 20 µm.

14. The method according to claim 1, wherein the support surface or receiving pocket are shaped to form the tissue into a medical implant in the form of a cardiovascular implant, a endovascular prostheses, an endoprostheses, a prosthetic heart valve, a TAVI/TAVR valve, an esophageal implant, a bile duct implant, a stent, a vascular stent, a drug eluting stent, a pulmonary valve stent, a bile duct stent, a peripheral stent, a mitral stent, a stent graft, a venous valve, a dental implant, a bone implant, a cochlear implant, an endopros- theses for closing persistent foramen ovale, an endoprosthe- ses for closing an atrial septal defect, a left atrial appendage closure device, a pacemaker, a leadless pacemaker or a defibrillator.

15. The method according to claim 1, wherein the tissue is collagen containing biological tissue.

16. The method according to claim 1, wherein the tissue is pericardial tissue.

17. A method for the preparation of crosslinked tissue, comprising:

providing tissue comprising chemically and/or biochemi- cally crosslinkable groups;

providing at least one permeable material layer configured to act as a support surface covering the tissue and/or a receiving pocket for the tissue;

placing the tissue on the support surface or in the receiv- ing pocket;

providing one or more pressure compensation layers, which are configured to partially or completely cover at least the tissue and the at least one permeable material layer;

chemically crosslinking the tissue with a suitable cross- linking agent; and removing of the crosslinked tissue from the support surface or the receiving pocket, wherein the at least one permeable material layer comprises two permeable material layers.

18. The method according to claim 17, wherein the two permeable material layers are bonded to each other.

19. The method according to claim 17, wherein the placing places the tissue between the two permeable layers.

20. A method for the preparation of crosslinked tissue, comprising:

providing tissue comprising chemically and/or biochemi- cally crosslinkable groups;

providing at least one permeable material layer configured to act as a support surface covering the tissue and/or a receiving pocket for the tissue;

placing the tissue on the support surface or in the receiv- ing pocket;

providing one or more pressure compensation layers, which are configured to partially or completely cover at least the tissue and the at least one permeable material layer;

chemically crosslinking the tissue with a suitable cross- linking agent for a period of at least 4 hours to a maximum of 5 days; and removing of the crosslinked tissue from the support surface or the receiving pocket.

21. A method for the preparation of crosslinked tissue, comprising:

providing tissue comprising chemically and/or biochemi- cally crosslinkable groups;

providing at least one permeable material layer configured to act as a support surface covering the tissue and/or a receiving pocket for the tissue;

placing the tissue on the support surface or in the receiv- ing pocket;

providing one or more pressure compensation layers, which are configured to partially or completely cover at least the tissue and the at least one permeable material layer;

chemically crosslinking the tissue with a suitable cross- linking agent;

removing of the crosslinked tissue from the support surface or the receiving pocket with a solution contain- ing surfactin and deoxycholic acid, and chemical post-crosslinking after the removing.

* * * * *